United States Patent
Orschel et al.

(10) Patent No.: US 10,030,964 B2
(45) Date of Patent: Jul. 24, 2018

(54) SYSTEMS AND METHODS FOR PERFORMING PHASE SHIFT INTERFEROMETRY WHILE A WAFER IS VIBRATING

(71) Applicant: SunEdison Semiconductor Limited, St. Peters, MO (US)

(72) Inventors: Benno Orschel, St. Louis, MO (US); Andrey Melnikov, Chesterfield, MO (US); John F. Valley, Lake Oswego, OR (US); Markus Jan Peter Siegert, Key West, FL (US)

(73) Assignee: SunEdison Semiconductor Limited (UEN201334164H), Singapore (SG)

( * ) Notice: Subject to any disclaimer, the term of this patent is extended or adjusted under 35 U.S.C. 154(b) by 0 days.

(21) Appl. No.: 15/534,550

(22) PCT Filed: Dec. 11, 2015

(86) PCT No.: PCT/US2015/065359
§ 371 (c)(1),
(2) Date: Jun. 9, 2017

(87) PCT Pub. No.: WO2016/094851
PCT Pub. Date: Jun. 16, 2016

(65) Prior Publication Data
US 2017/0363413 A1    Dec. 21, 2017

Related U.S. Application Data

(60) Provisional application No. 62/091,170, filed on Dec. 12, 2014.

(51) Int. Cl.
*G01B 11/30* (2006.01)
*G01B 9/02* (2006.01)
(Continued)

(52) U.S. Cl.
CPC ....... *G01B 9/02077* (2013.01); *G01B 9/0201* (2013.01); *G01B 9/02083* (2013.01); *G01B 11/2441* (2013.01); *G01N 21/9501* (2013.01)

(58) Field of Classification Search
CPC ..... G01B 11/25; G01B 11/30; G01B 11/2441; G01B 9/02088; G01B 9/0209
See application file for complete search history.

(56) References Cited

U.S. PATENT DOCUMENTS 5,473,434 A * 12/1995 de Groot ............ G01B 11/2441
356/514
7,289,225 B2 * 10/2007 De Groot ........... G01B 11/0675
356/497

(Continued)

FOREIGN PATENT DOCUMENTS

GB        2497098 A     6/2013

OTHER PUBLICATIONS de Groot, Peter J. "Vibration in Phase-shifting Interferometry," Journal of the Optical Society of America A, 12(2): 354-365 (1995).

(Continued)

*Primary Examiner* — Jonathan Hansen
(74) *Attorney, Agent, or Firm* — Armstrong Teasdale LLP

(57) ABSTRACT

A method performs phase shift interferometry to detect irregularities of a surface of a wafer after the wafer has been placed into an interferometer and while the wafer is vibrating. Additionally, a system and a non-transitory computer-readable storage medium have computer-executable instructions embodied thereon for performing phase shift interferometry to detect irregularities of a surface of a wafer after the wafer has been placed into an interferometer and while the wafer is vibrating.

20 Claims, 19 Drawing Sheets

(51) Int. Cl.
*G01B 11/24* (2006.01)
*G01N 21/95* (2006.01)

(56) References Cited

U.S. PATENT DOCUMENTS

2010/0118312 A1* 5/2010 Deck .................. G01B 11/2441
356/450
2014/0343893 A1* 11/2014 Mansfield ............ G01B 11/303
702/167

OTHER PUBLICATIONS

International Search Report and Written Opinion issued for PCT/US2015/065359, dated Apr. 29, 2016.

* cited by examiner

1000

SYSTEMS AND METHODS FOR PERFORMING PHASE SHIFT INTERFEROMETRY WHILE A WAFER IS VIBRATING

CROSS-REFERENCE TO RELATED APPLICATIONS

This application is a 35 U.S.C. § 371 National Stage application of International Application No. PCT/US2015/065359, filed Dec. 11, 2015, which claims the benefit of U.S. Provisional Application No. 62/091,170, filed Dec. 12, 2014, both of which are incorporated herein by reference in their entirety.

FIELD

The field relates generally to detecting irregularities on the surface of an object, and more particularly to systems and methods for detecting irregularities on a surface of a vibrating object.

BACKGROUND

In at least some known systems, when a wafer, for example a silicon wafer, is placed in a Fizeau interferometer for analysis, the placement of the wafer causes the wafer to vibrate. It is possible to perform Fourier based phase shift interferometry to suppress measurement errors caused by vibrations of the wafer, but the large amount of numerical processing required for such Fourier based phase shift interferometry makes such an approach impractical. In contrast, some known systems perform phase shift interferometry using a limited set of wavelengths distributed over one interference period. By reducing the number of wavelengths in the set, the accuracy of the phase shift interferometry is similarly reduced, while processing speed is increased. In other systems for suppressing errors from residual vibrations of the wafer, a wavelength is continuously scanned. During the wavelength scan, a camera captures a series of images, producing reference wavelength images for an algorithm designed for a limited set of wavelengths. However, exposure is timed in such a way that each reference image is an integral (i.e., in-camera integration) of a periodically-changing interference signal. In addition, the image capture process is repeated a predefined number of times (i.e., n-times). Subsequently, the sets of images are averaged before applying the algorithm designed for the limited wavelength set. In-camera integration and n-times averaging suppress image sensor noise and residual vibration of the wafer. However, this approach still suffers from an inherent lack of numerical accuracy, due to the reliance on an algorithm designed for use with a limited wavelength set. Additionally, the approach requires waiting an indefinite amount of time for the vibrations of the wafer to stop before performing image capture. Known systems have no ability to detect the quality of data or level of vibrations. Another drawback of such systems is the need for absolute wavelength calibration, to enable the n-times averaging, as even a relatively slight wavelength miscalibration may result in relatively significant numerical errors.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

In one aspect, a method for performing phase shift interferometry to detect irregularities of a surface of a wafer after the wafer has been placed into an interferometer and while the wafer is vibrating is disclosed. The method includes emitting a beam of light at each of a plurality of wavelengths at a reference plane of the interferometer and at the wafer. The method additionally includes exposing an image capture device to reflected light from the reference plane and the wafer for each of a plurality of captured image samples, to generate an exposed signal. Additionally, the method includes cyclically fitting, by at least one computing device, a fitted signal to the exposed signal while the wafer is vibrating. The method additionally includes cyclically determining, by at least one computing device, a level of vibration of the wafer, based at least in part on the exposed signal. Additionally, the method includes determining, by at least one computing device, irregularities in the surface of the wafer when reductions in the vibration are below a predefined threshold, based on the fitted signal.

In another aspect, a system comprising at least one computing device coupled to an interferometer is disclosed. The interferometer includes a light source, a reference plane located opposite the light source, a beam splitter located between the light source and the reference plane, and an image capture device configured to receive light from the beam splitter. The at least one computing device is configured to perform phase shift interferometry to detect irregularities of a surface of a wafer after the wafer has been placed into the interferometer and while the wafer is vibrating. More specifically, the at least one computing device is configured to cause the light source to emit a beam of light at each of a plurality of wavelengths at the reference plane and at the wafer. Additionally, the at least one computing device is configured to cause the image capture device to be exposed to reflected light from the reference plane and the wafer for each of a plurality of captured image samples, to generate an exposed signal. Additionally, the at least one computing device is configured to cyclically fit a fitted signal to the exposed signal while the wafer is vibrating. Additionally, the at least one computing device is configured to cyclically determine a level of vibration of the wafer, based at least in part on the exposed signal, and determine irregularities in the surface of the wafer when reduction in the vibrations are below a predefined threshold, based on the fitted signal.

In another aspect, a non-transitory computer-readable storage medium having computer-executable instructions embodied thereon is disclosed. The computer-executable instructions are for performing phase shift interferometry to detect irregularities of a surface of a wafer after the wafer has been placed into an interferometer and while the wafer is vibrating. When executed by at least one computing device in a system that includes the at least one computing device coupled to the interferometer including a light source, a reference plane located opposite the light source, a beam splitter located between the light source and the reference plane, and an image capture device configured to receive light from the beam splitter, the computer-executable instructions cause the at least one computing device to cause the light source to emit a beam of light at each of a plurality of wavelengths at the reference plane and at the wafer. Additionally, the computer-executable instructions cause the at least one computing device to cause the image capture device to be exposed to reflected light from the reference plane and the wafer for each of a plurality of captured image samples, to generate an exposed signal. Additionally, the computer-executable instructions cause the at least one computing device to cyclically fit a fitted signal to the exposed signal while the wafer is vibrating. Additionally, the computer-executable instructions cause the at least one computing device to cyclically determine a level of vibration of the wafer, based at least in part on the exposed signal, and determine irregularities in the surface of the wafer when reductions in the vibration are below a predefined threshold, based on the fitted signal.

In another aspect, a method for detecting irregularities of a surface of an object while the object is vibrating is disclosed. The method includes projecting a moving fringe pattern to the surface of the object. The method additionally includes exposing an image capture device to the moving fringe pattern for each of a plurality of captured image samples to generate an exposed signal. Additionally, the method includes cyclically fitting, by at least one computing device, a fitted signal to the exposed signal while the object is vibrating. The method additionally includes cyclically determining, by at least one computing device, a level of vibration of the object, based at least in part on the exposed signal and determining, by at least one computing device, irregularities in the surface when reductions in the vibration are below a predefined threshold, based on the fitted signal.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Figure 1:
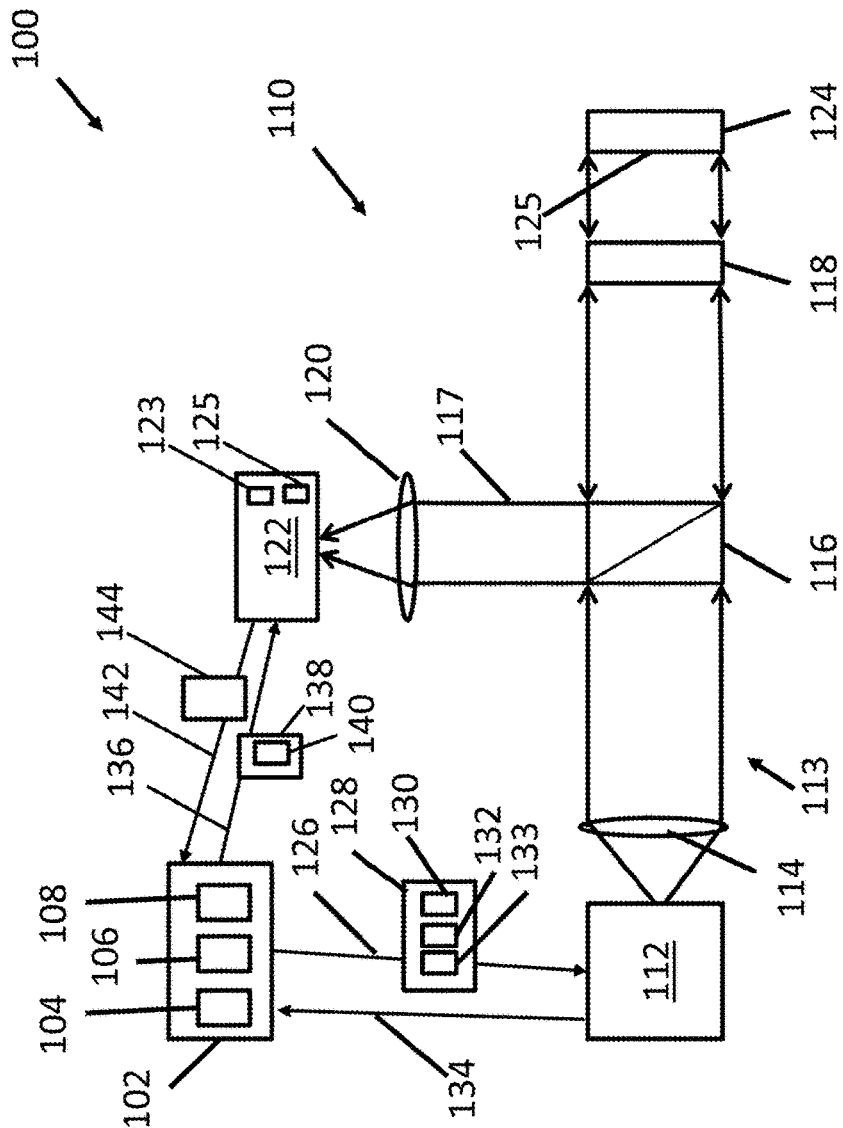
FIG. 1 is a diagram of an example system for performing phase shift interferometry to detect irregularities on a surface of a wafer.

FIG. 1 is a diagram of a system 100 for performing phase shift interferometry ("PSI") to detect irregularities on a surface 125 of a wafer 124. System 100 includes an analyzer device 102 and an interferometer 110. Analyzer device 102 includes a plurality of computing devices, including a first computing device 104, a second computing device 106, and a third computing device 108. In other implementations, analyzer device 102 includes a different number of computing devices. Interferometer 110, which in at least some implementations, is a Fizeau interferometer, includes a light source 112, a first lens 114, a beam splitter 116, a reference plane 118, a second lens 120, and an image capture device 122, such as a camera. In operation, wafer 124, which is for example a silicon wafer, is placed opposite light source 112.

Reference plane 118, which is semi reflective, is disposed between light source 112 and wafer 124. Beam splitter 116 is disposed between light source 112 and reference plane 118. During operation of system 100, light source 112 emits a light beam 113, which passes through first lens 114. A first portion of light beam 113 is reflected by reference plane 118. A second portion is transmitted through semi-reflective reference plane 118 and reflected by surface 125 of wafer 124. Beam splitter 116 directs the reflected light 117 (e.g., the first portion and the second portion) towards image capture device 122. The reflected light 117 passes through second lens 120 to image capture device 122 which samples reflected light 117.

Analyzer device 102 is communicatively coupled to light source 112 and image capture device 122. More specifically, analyzer device 102 transmits light source instruction signals 126 to light source 112. Light source instruction signals 126 include light source instructions 128. Light source instructions 128 include a control function for cyclically emitting different wavelengths 130, for example as a function of time and/or a number of samples that have been obtained. In some implementations, wavelengths 130 is a range or set of wavelengths, and instructions 128 additionally include a currently selected wavelength 132, and a time period 133 during which light 113 is to be emitted at each of the wavelengths 130. Accordingly, light source 112 cycles through wavelengths 130, starting with selected wavelength 132, and emits each wavelength 130 for the time period 133. In at least some implementations, light source 112 transmits a response signal 134, for example acknowledging receipt of light source instruction signal 126.

Analyzer device 102 transmits image capture instruction signals 136 to image capture device 122. Image capture instruction signals 136 include image capture instructions 138. Image capture instructions 138 include an exposure time 140, representing an amount of time that image capture device 122 is to receive reflected light 117 to generate a sample 144. Image capture device 122 transmits image signals 142 to analyzer device 102. Image signals 142 include samples 144 generated by image capture device 122 by receiving reflected light 117 during exposure time 140. As described in more detail, image capture device 122 repeatedly captures reflected light 117 during repeated exposure times 140. Additionally, image capture device 122 performs the capture of reflected light 117 for each of a plurality of light sensors 123, for example charge coupled devices (CCDs), included in image capture device 122. Light sensors 123 are associated with respective pixels 125, described in more detail herein. While system 100 includes an interferometer 110, other implementations do not include interferometer 110 and instead project a moving fringe pattern (e.g., light 117) onto surface 125, as described in more detail herein.

Figure 2:
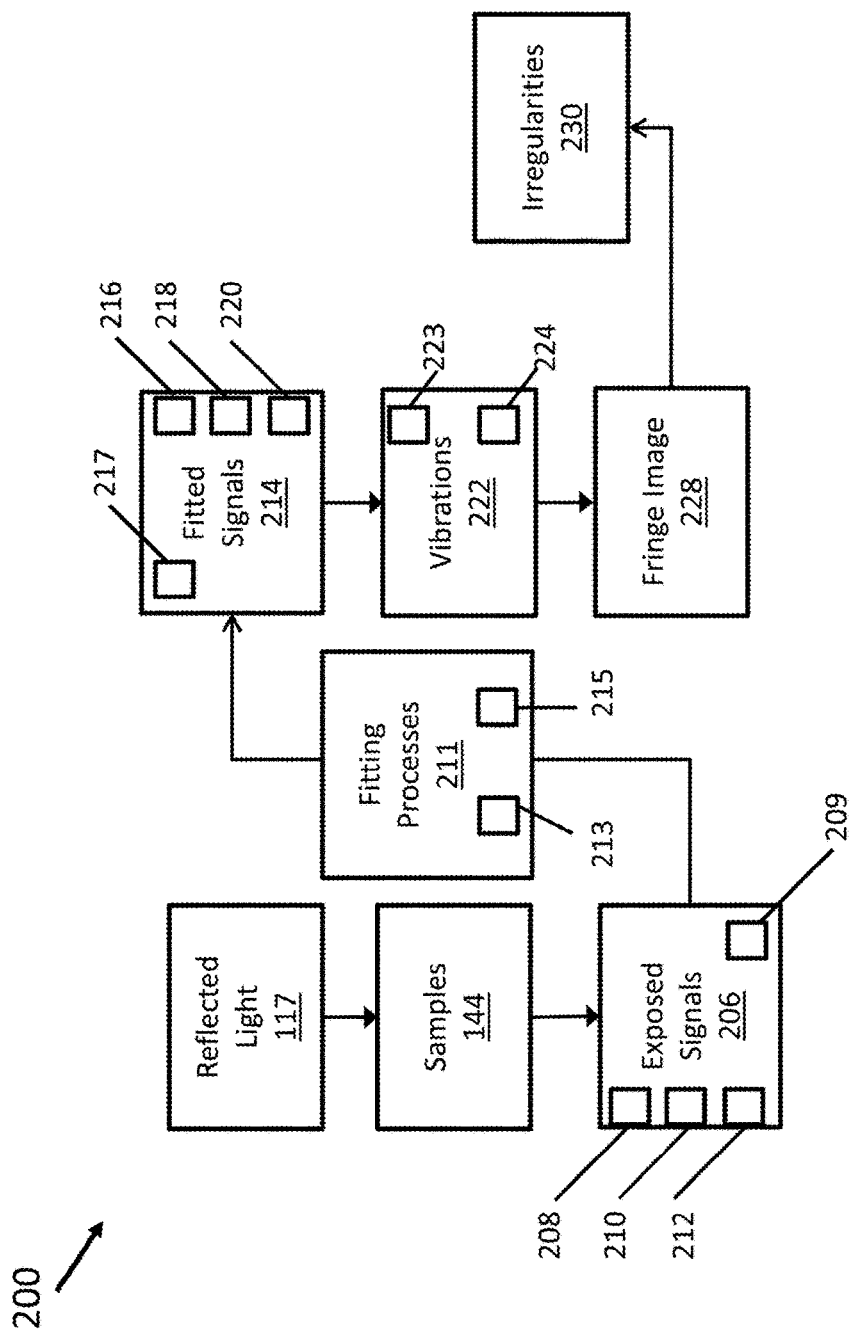
FIG. 2 is a flow diagram illustrating a relationship between reflected light and irregularities detected on the surface of the wafer of FIG. 1.

FIG. 2 is a flow diagram illustrating a relationship between reflected light 117 and irregularities 230 detected on the surface 125 of the wafer 124. Reflected light 117 is received by image capture device 122 at a rate defined by exposure time 140. For example, in some implementations, image capture device 122 operates at fifteen frames per second. Accordingly, exposure time 140 is one fifteenth of a second. Image capture device 122 generates a sample 144 from reflected light 117 for each light sensor 123. As image capture device 122 generates and transmits samples 144 to analyzer device 102, light source 112 cycles through wavelengths 130. A series of samples 144, for example 300 samples, represents an exposed signal 206. Each exposed signal 206 has a plurality of properties, including a phase 208, a rate of change in phase 209, an amplitude 210, and an offset 212 (e.g., a y-offset). Using fitting processes 211, analyzer device 102 fits fitted signals 214 to exposed signals 206.

Fitting processes 211 include a moving window process 213 and an infinite response filter 215, both are which are described in more detail herein. Each fitted signal 214 has a plurality of properties, including a phase 216, a rate of change in phase 217, an amplitude 218, and an offset 220 (e.g., a y-offset). Fitted signals 214 reduce or eliminate noise due, for example, to vibrations 222 of wafer 124. As described herein, different implementations of system 100 fit fitted signals 214 to exposed signals 206 using different methods. Additionally, as described herein, analyzer device 102 determines that fitted signals 214, each associated with a respective pixel 125 and each having an intensity, are to be used to generate a fringe image 228 when an amplitude 223 of vibrations 222 of wafer 124 have dampened below a predefined threshold or converged to a constant vibration (i.e., the rate of change in phase 217 has dropped below a predefined threshold 224). In at least some implementations, predefined threshold 224 is greater than zero. Fringe image 228 represents irregularities 230 in the surface 125 of wafer 124, based on fitted signals 214.

Figure 3:
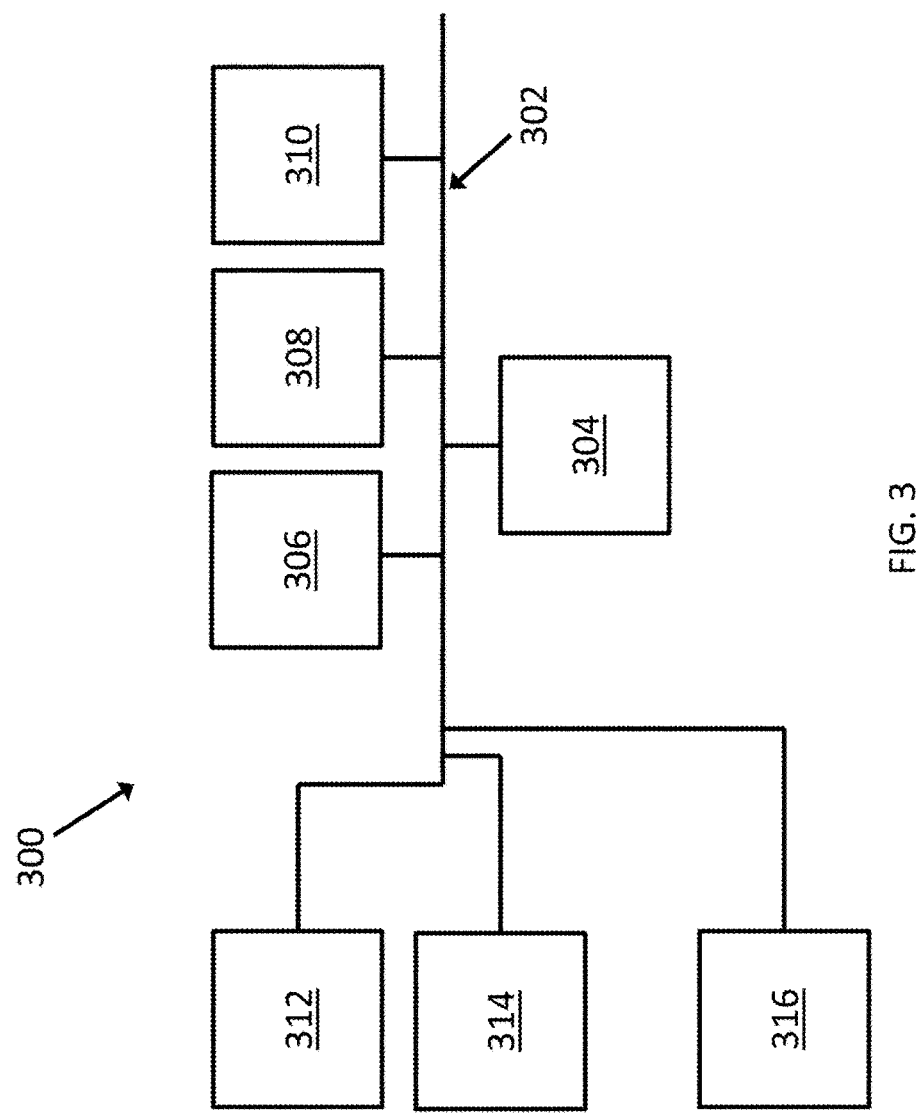
FIG. 3 is a block diagram of an example computing device that may be used in the system of FIG. 1.

FIG. 3 is a schematic diagram of an example computing device 300. Computing device 300 is representative of first computing device 104, second computing device 106, third computing device 108, analyzer device 102, light source 112, and image capture device 122. More specifically, each of first computing device 104, second computing device 106, third computing device 108, analyzer device 102, light source 112, and image capture device 122 includes one or more components of computing device 300. Computing device 300 includes a bus 302, at least one processor 304, a memory 306, a read only memory (ROM) 308, a storage device 310, an input device 312, an output device 314, and a communication interface 316. Bus 302 may include a path that permits communication among the components of computing device 300.

Processor 304 may include any type of processor, microprocessor, or processing logic that interprets and executes instructions. Memory 306 may include a random access memory (RAM) or another type of dynamic storage device that stores information and instructions for execution by processor 304. ROM 308 may include a conventional ROM device or another type of static storage device that stores static information and instructions for use by processor 304. Storage device 310 may include a magnetic and/or optical recording medium and its corresponding drive.

Input device 312 may include a mechanism that permits computing device 300 to receive commands, instructions, or other inputs from a user, including visual, audio, touch, button presses, stylus taps, etc. Accordingly, input device 312 may include, for example, a microphone, one or more buttons, and/or a touch screen. Output device 314 may include a mechanism that outputs information to the user, including a display (including a touch screen) and/or a speaker. Communication interface 316 may include any transceiver-like mechanism that enables computing device 300 to communicate with other devices and/or systems.

As described herein, computing device 300 performs operations in response to processor 304 executing software instructions contained in a computer-readable medium, such as memory 306. A computer-readable medium may be defined as a physical or logical memory device and/or carrier wave. The software instructions may be read into memory 306 from another computer-readable medium, such as data storage device 310, or from another device via communication interface 316. The software instructions contained in memory 306 may cause processor 304 to perform processes described herein. In other implementations, hardwired circuitry may be used in place of or in combination with software instructions to implement processes consistent with the subject matter herein. Thus, implementations consistent with the principles of the subject matter disclosed herein are not limited to any specific combination of hardware circuitry and software.

Figure 4:
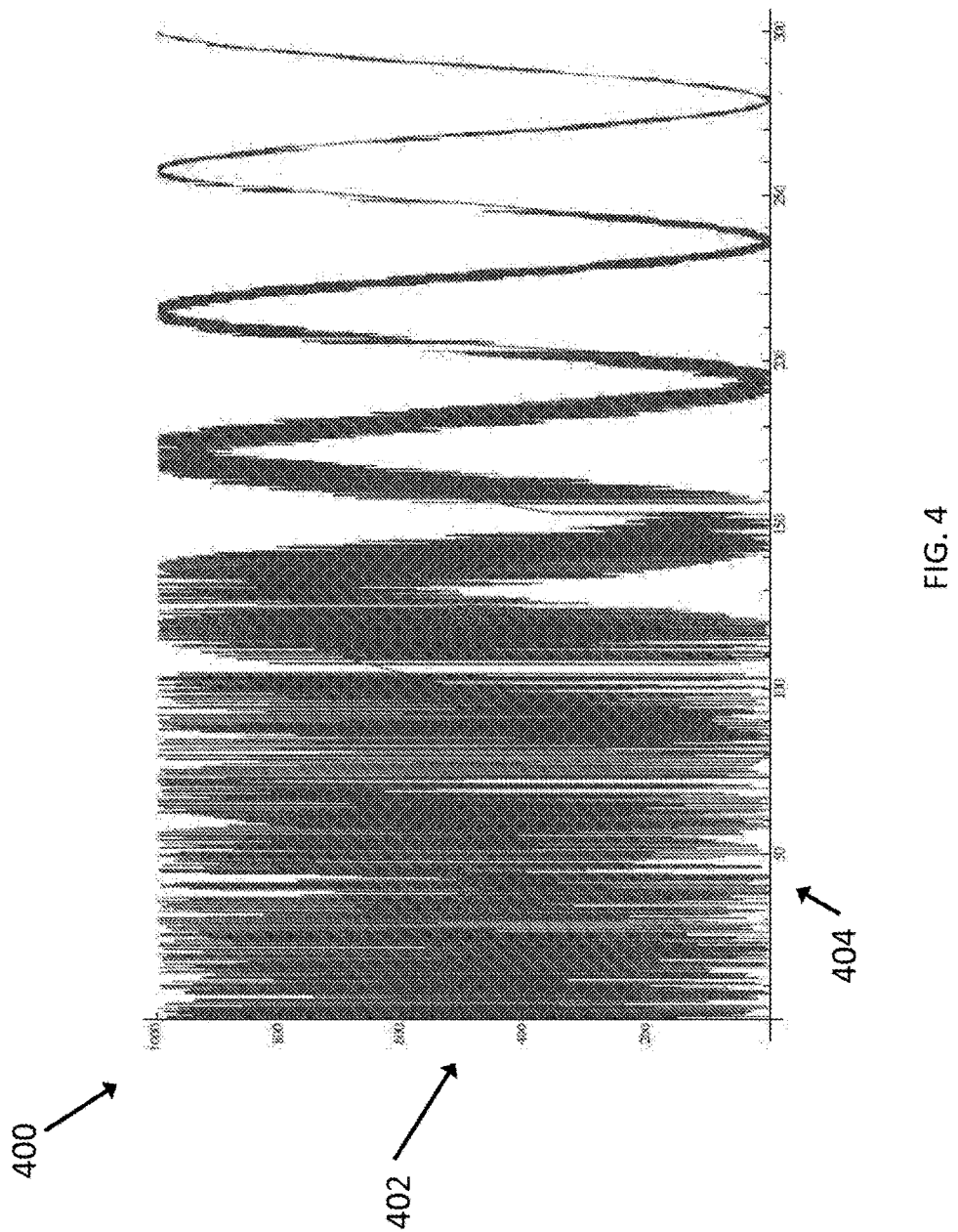
FIG. 4 is a plot of dampening vibrations of the wafer shown in FIG. 1.

After wafer 124 has been placed in interferometer 110, vibrations of wafer begin to dampen. Light captured by image capture device 122 (e.g., reflected light 117) is represented in plot 400 shown in FIG. 4, in which light intensity is represented by y-axis 402 and sample numbers (e.g., samples 144) are represented by x-axis 404. Initially, the amplitude of the vibrations 222 of wafer 124 is one micrometer and the frequency is 402 vibrations per second. Interfered light (e.g., reflect light 117) enters image capture device 122 and image capture device 122 is exposed for a predefined amount of time (e.g., exposure time 140), generating samples 144. The exposure is equivalent to a numeric integral of a time signal.

Figure 5:
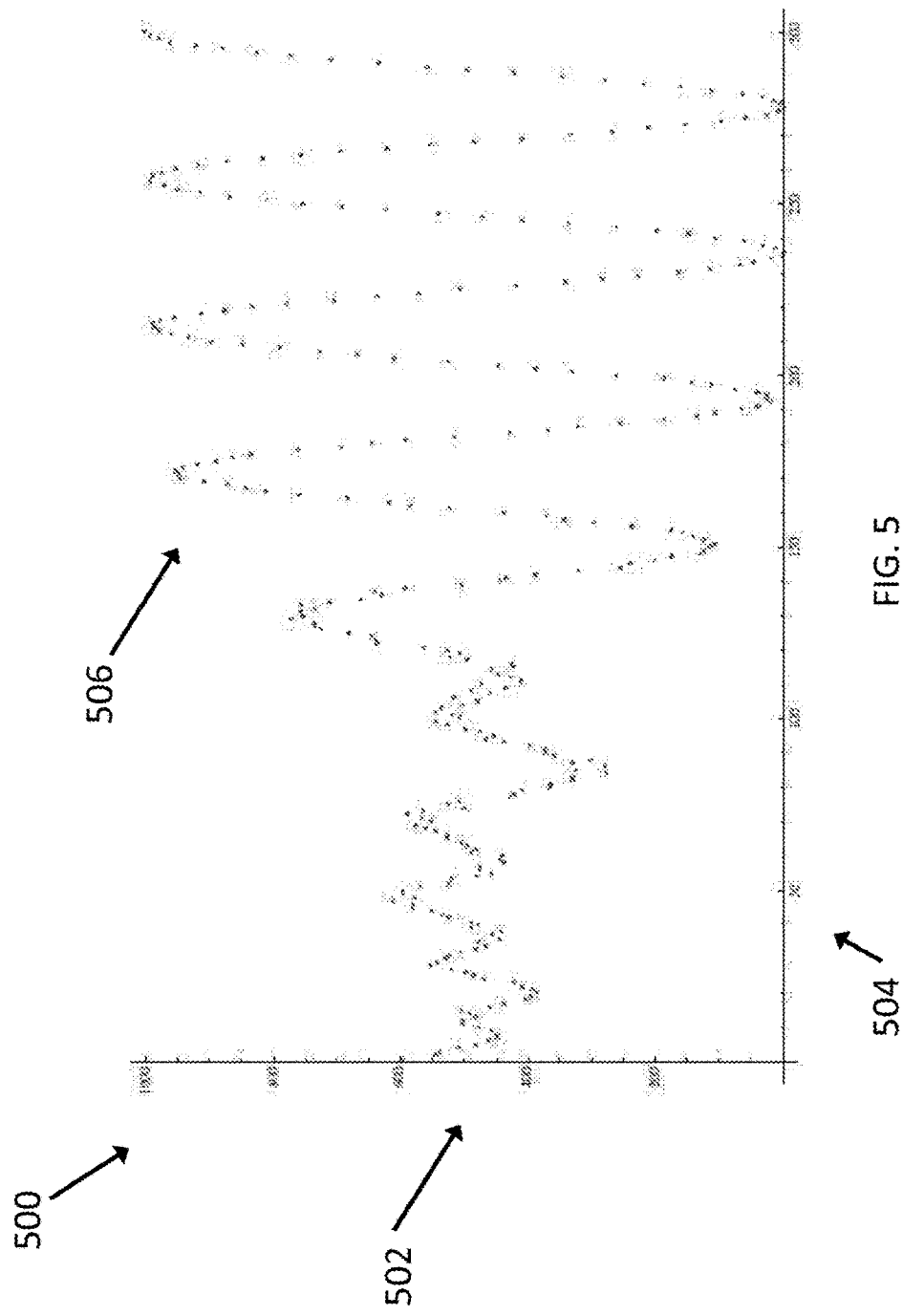
FIG. 5 is a plot of intensities of reflected light in samples generated by an image capture device included in the system of FIG. 1.

FIG. 5 is a plot 500 of light intensity, represented by y-axis 502, and sample numbers (e.g., samples 144), represented by x-axis 504. As described above, the wavelengths (e.g., wavelengths 130) of light emitted by light source 112 are cycled as image capture device 122 generates samples 144. The resulting set of samples 144 forms an exposed signal 506. In at least some implementations, image capture device 122 operates at fifteen frames per second, meaning for each light sensor 123, image capture device 122 generates fifteen samples per second. In such implementations, image capture device 122 generates exposed signal 506, which includes 300 samples, in twenty seconds. Exposed signal 506 includes noise having an amplitude of about five units of intensity (i.e., y-axis 502).

Figure 6:
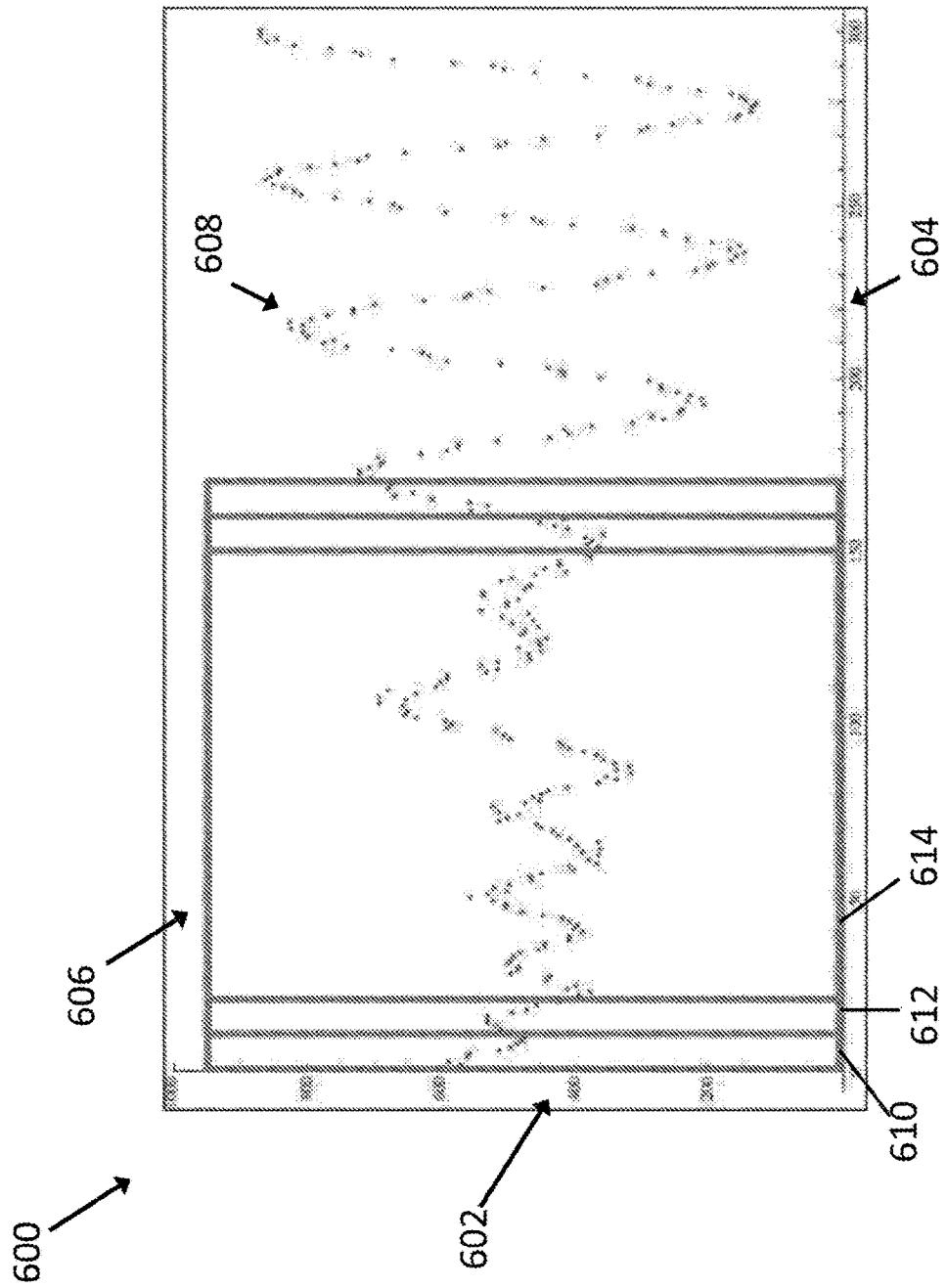
FIG. 6 is a plot of intensities of reflected light in samples generated by an image capture device included in the system of FIG. 1, and a moving window used to analyze an exposed signal formed from the samples.

FIG. 6 is a plot 600 of light intensity, represented by y-axis 602, and sample numbers (e.g., samples 144), represented by x-axis 604, and a window 606 for analyzing an exposed signal 608 formed from the samples 144. More specifically, analyzer device 102 implements moving window process 213 to fit a fitted signal (e.g., fitted signal 214) to exposed signal 608. Window 606 is a set of memory 306 that includes 300 samples 144. Window 606 starts at a first position 610 and moves to additional positions, including a second position 612, and a third position 614. For first position 610, analyzer device 102 performs a complete or "full" Fourier analysis of a first set of 300 samples 144 included in window 606, to fit a fitted signal (e.g., fitted signal 214) to exposed signal 608.

Next, for second position 612, analyzer device 102 performs a partial Fourier integral on a second set of 300 samples that includes a predefined number of samples (e.g., twenty samples) generated after the first set of samples, and excludes the same predefined number of the earliest samples from the first set. Likewise, for third position 614, analyzer device 102 performs an additional partial Fourier integral on a third set of 300 samples that includes the predefined number of samples generated after the second set of samples, and excludes the same predefined number of the earliest samples from the second set. Accordingly, as window 606 moves from position to position, a portion of the samples within the window 606 stay the same, while the samples on the edges (e.g., beginning and ending of window 606) change. Analyzer device 102 stores samples 144 in sections ("buckets") of memory 306 that are sized to store the predefined number of samples used to move from position to position. More specifically, if the predefined number of samples is twenty, then each section of memory (each bucket) holds twenty samples and window 606 covers fifteen sections ("buckets") of memory at a time, for a total of 300 samples. While three positions (e.g., first position 610, second position 612, and third position 614) are shown, analyzer device 102 moves window 606 through a different number of positions in other implementations.

For first position 610, analyzer device 102 attempts to fit a signal (e.g., fitted signal 214) of the form given by Equation 1:

$$a + b\sin\left(\frac{4\pi G}{\lambda_i}\right) + c\cos\left(\frac{4\pi G}{\lambda_i}\right) \quad \text{(Equation 1)}$$

More specifically, the fitted signal 214 generated using Equation 1 approximates a version of exposed signal 608 without any noise due to vibrations 222 of wafer 124. In at least some implementations, values of $\lambda_i$ are in the range of 635 nanometers to 635.012 nanometers, changing linearly so that exactly three fringes of a wave are detected.

As described above, window 606 covers 300 samples, each $y_i$. The error, which analyzer device 102 attempts to minimize, is given by Equation 2:

$$\sum \left[y_i - a - b\sin\left(\frac{4\pi G}{\lambda_i}\right) - c\cos\left(\frac{4\pi G}{\lambda_i}\right)\right]^{\wedge}2 \quad \text{(Equation 2)}$$

Accordingly, analyzer device 102 applies a maximum likelihood algorithm as follows. Analyzer device 102 sets the partial derivatives of the change in error and the change in each of a, b, and c equal to zero, as shown in Equation 3.

$$\frac{\partial \text{error}}{\partial a} = \frac{\partial \text{error}}{\partial b} = \frac{\partial \text{error}}{\partial c} = 0 \quad \text{(Equation 3)}$$

Analyzer device 102 performs the above calculations for each value of G in a predefined range of values. Given that the values of $\lambda_i$ are almost constant, ranging from 635 nanometers to 635.012 nanometers, and trigonometric functions are periodic, the calculations give the same result for $\Delta G = \lambda/2$.

Figure 7:
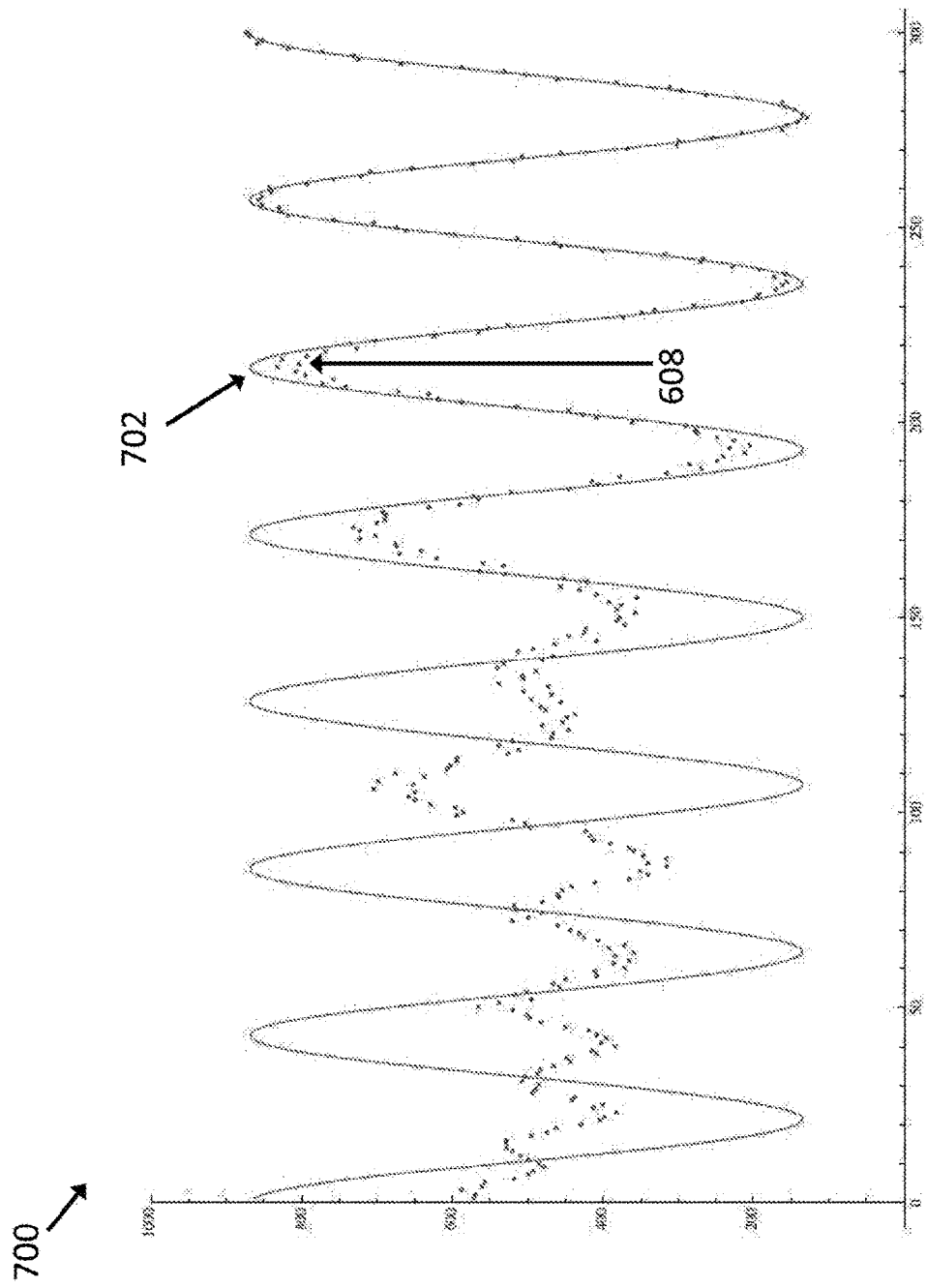
FIG. 7 is a plot of the exposed signal of FIG. 6 and a fitted signal generated by the system of FIG. 1.
Figure 8:
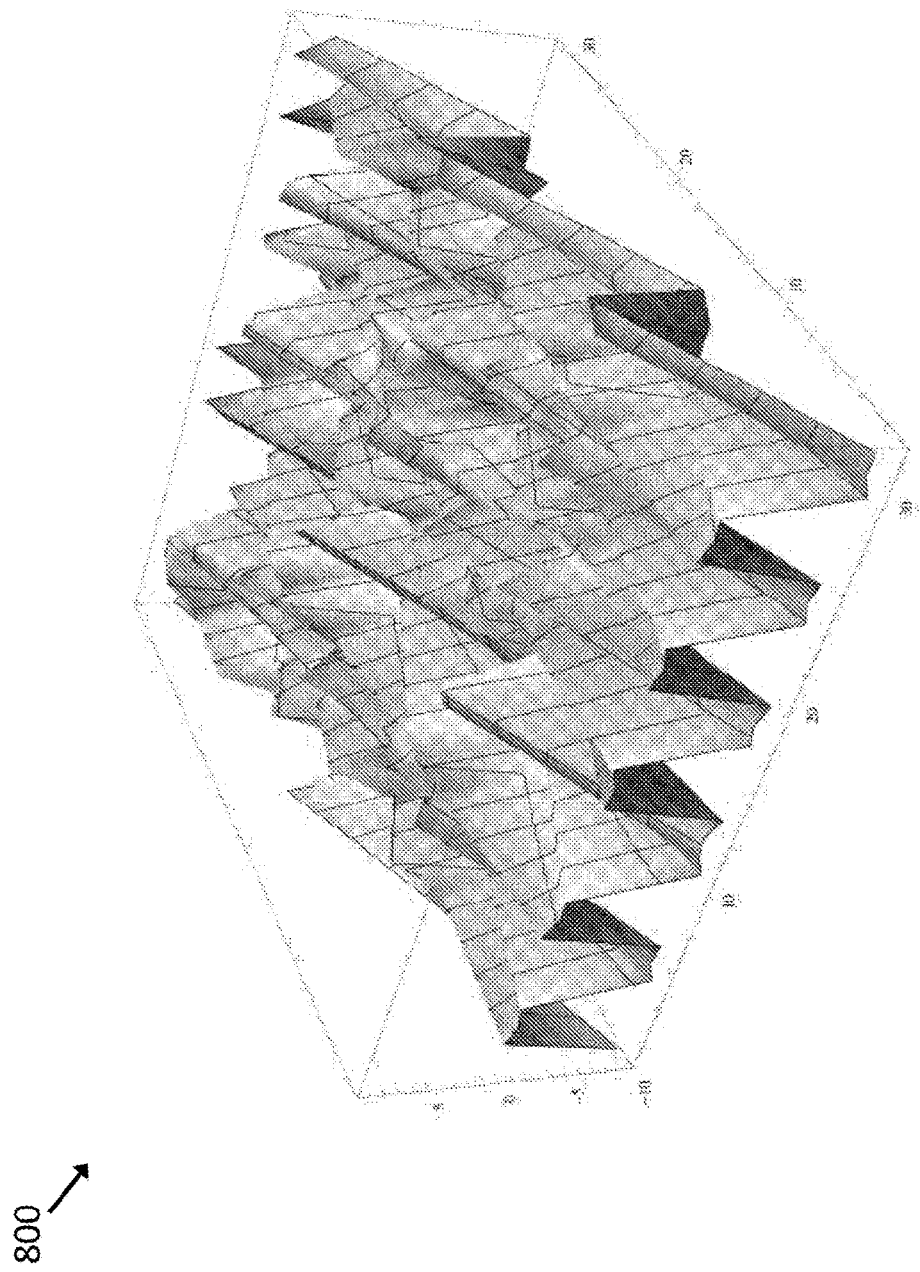
FIG. 8 is a three dimensional graph of an actual topology of the surface of the wafer in the system of FIG. 1.
Figure 9:
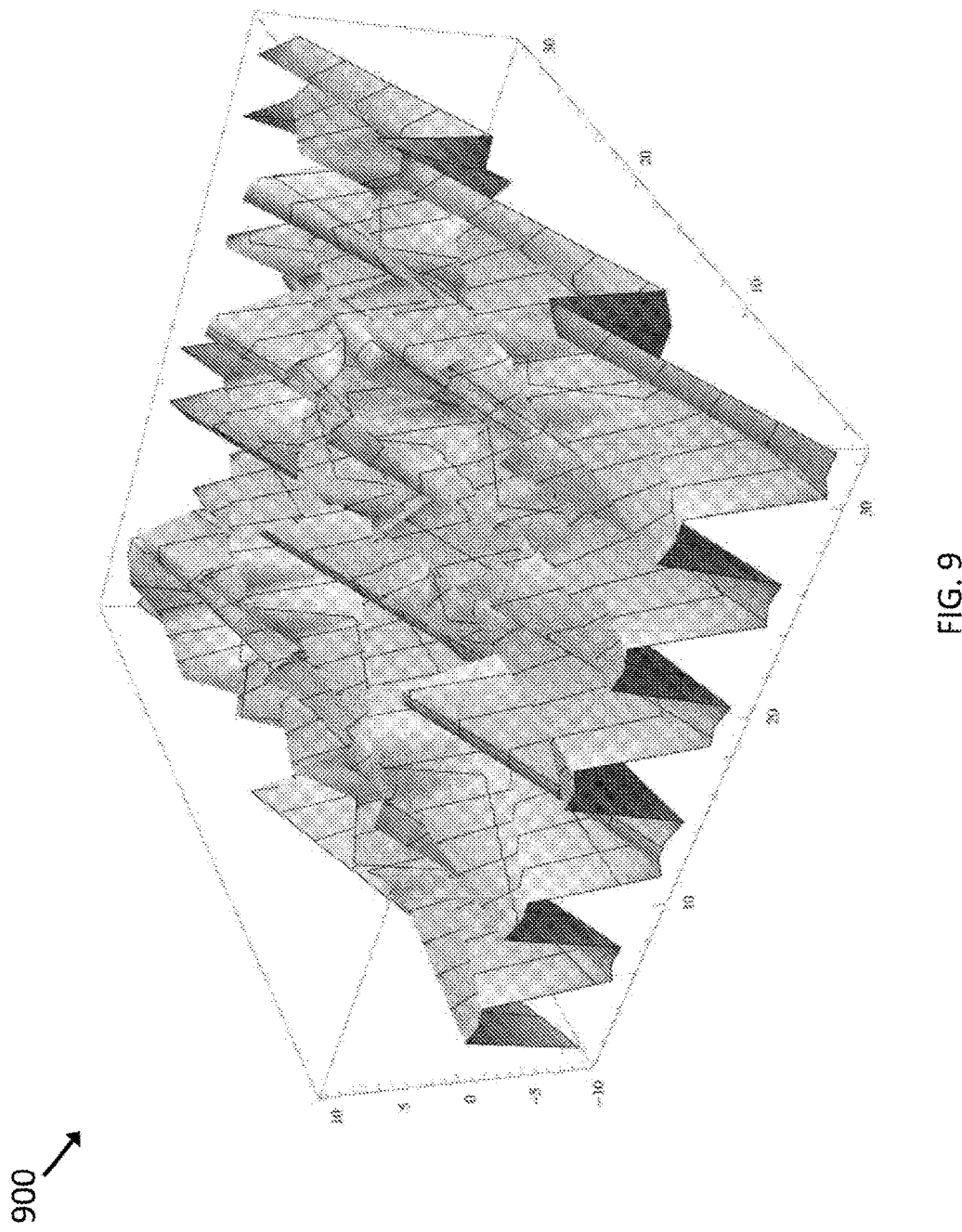
FIG. 9 is a three dimensional graph of an estimated topology of the surface of the wafer using fitted signals.
Figure 10:
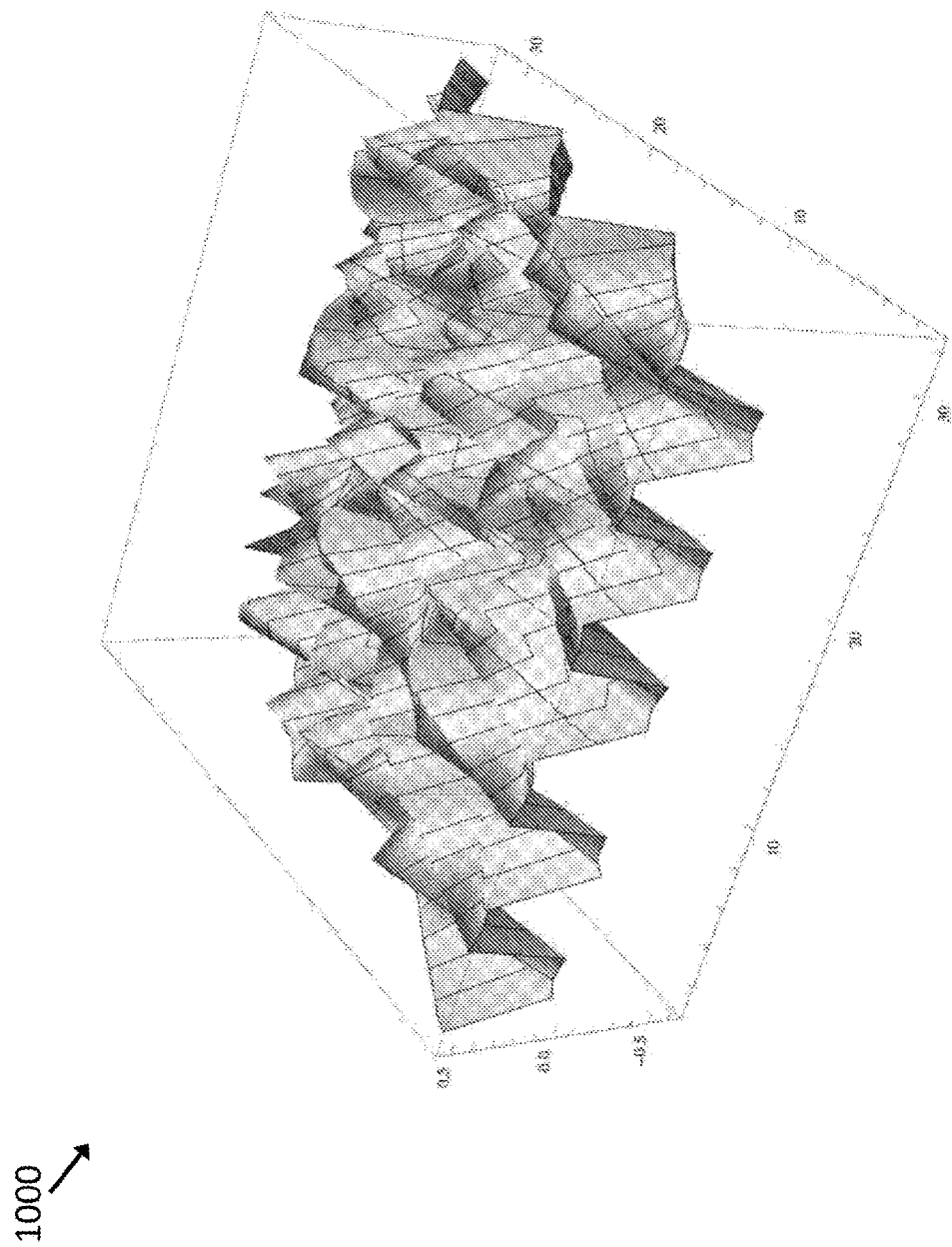
FIG. 10 is a three dimensional graph of differences (i.e., error) between the graph of FIG. 8 and the graph of FIG. 9.

FIG. 7 is a plot 700 of the exposed signal 608 and a fitted signal 702 generated by analyzer device 102 using the process described above. The phase (e.g., phase 216) of the fitted signal 702 matches the phase (e.g., phase 208) of the exposed signal 608. FIG. 8 is a three dimensional graph 800 of an actual topology (irregularities) of surface 125 of wafer 124, measured in nanometers. Wafer 124 is 32 nanometers by 32 nanometers, and irregularities in the surface 125 range from −10 nanometers to 10 nanometers into wafer 124. FIG. 9 is a three dimensional graph 900 of an estimated topology of the surface 125 of wafer 124 generated using processes described above. More specifically, analyzer device 102 generates graph 900 using fitted signals 214, similar to fitted signal 702, for each pixel 125. That is, graph 900 is generated from intensities of the pixels 125. FIG. 10 is a three dimensional graph 1000 of differences (i.e., error) between graph 800 and the graph 900. As shown, the error is, at most, 0.5 nanometers.

In some implementations, rather than fitting a signal using Equation 1, analyzer device 102 uses the form shown in Equation 4.

$$a + \left(1 - de^{-\frac{i}{\tau}}\right)\left[b\sin\left(\frac{4\pi G}{\lambda_i}\right) + c\cos\left(\frac{4\pi G}{\lambda_i}\right)\right] \quad \text{(Equation 4)}$$

A fitted signal 214 generated using Equation 4 approximates a version of exposed signal 608 without any noise due to vibrations 222 of wafer 124 and, in addition to matching the phase 208 of the exposed signal 608, the fitted signal 214 also matches the amplitude of vibrations 222 as vibrations 222 dampen over time. Analyzer device 102 performs an optimization function to select a value of τ. More specifically, analyzer device 102 selects a value of τ that minimizes the resulting error from Equation 4 (i.e., where the change in error over the change in τ is zero).

Analyzer device 102 uses a maximum likelihood algorithm as follows. Analyzer device 102 sets the partial derivatives of the change in error and the change in each of a, b, c, and d equal to zero, as shown in Equation 5.

$$\frac{\partial \text{error}}{\partial a} = \frac{\partial \text{error}}{\partial b} = \frac{\partial \text{error}}{\partial c} = \frac{\partial \text{error}}{\partial d} = 0 \quad \text{(Equation 5)}$$

Figure 11:
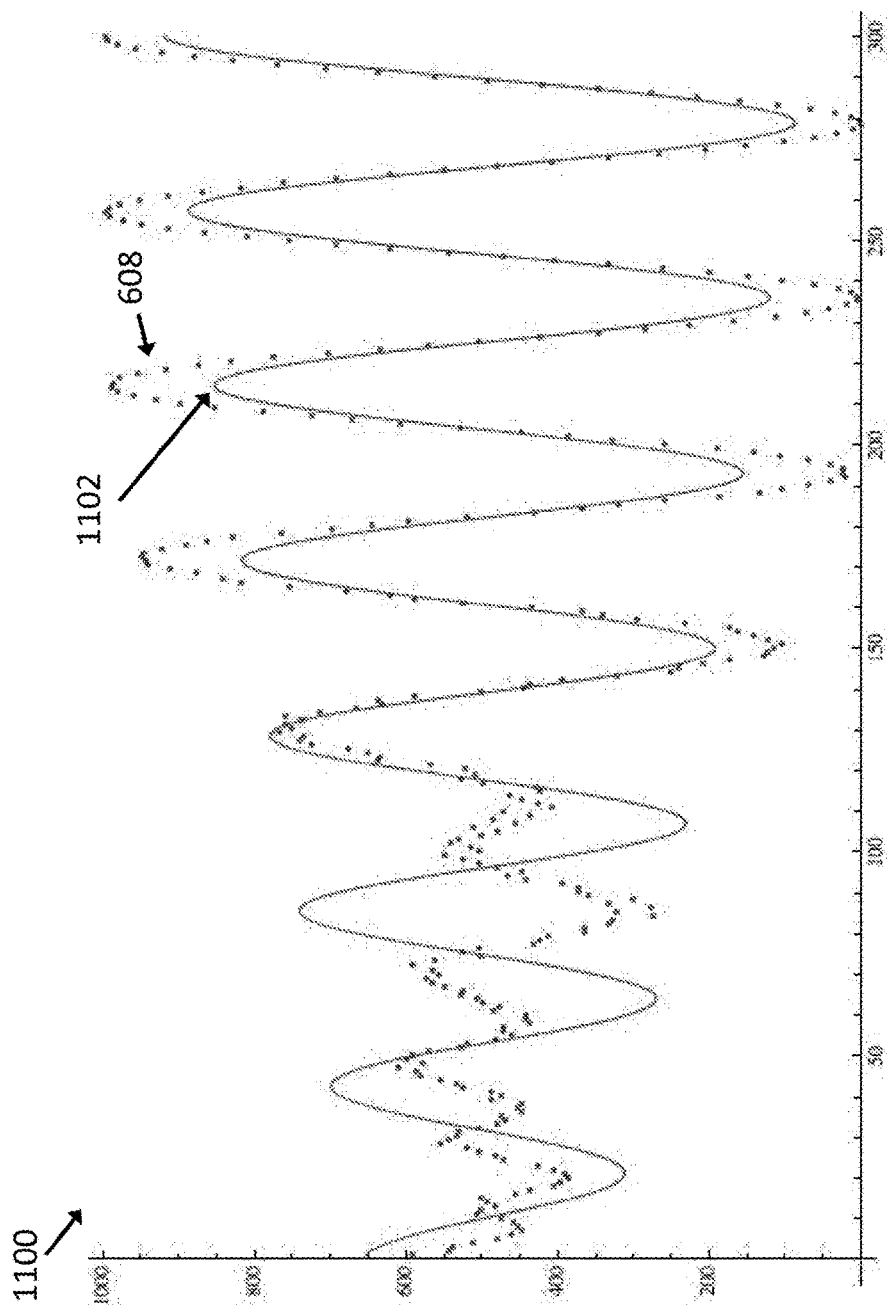
FIG. 11 is a plot of the exposed signal of FIG. 6 and a second fitted signal generated by the system of FIG. 1.

Given that the dependence on a, b, c, and d is more complicated than in Equation 1, analyzer device 102 solves for a, b, and c as a function of d. Then analyzer device 102 deduces a seventh degree polynomial equation on d and detects that the equation reaches zero for a value of d between zero and one. Analyzer device 102 then inserts the value of d and solves for the values of a, b, and c. Analyzer device performs the above process for the value of τ described above and for a fixed value of G. FIG. 11 is a plot 1100 showing exposed signal 608 and a fitted signal 1102 generated using the process described above. The amplitude 218 of fitted signal 1102 more closely matches the amplitude 210 of exposed signal 608, as compared to the fitted signal 702 (FIG. 7) generated using Equation 1.

In another implementation, analyzer device 102 generates a fitted signal 214 using infinite response filter 215, and more specifically, a harmonic filter, having a form shown in Equation 8.

$$y = a + b\,\sin(kw) + c\,\cos(kw) \quad \text{(Equation 8)}$$

The fitted signal 214 approximates a version of an exposed signal 206 without noise from vibrations 222 of wafer 124. In Equation 8, the following value of w, given by Equation 9, corresponds to a basic harmony.

$$w = \frac{4\pi}{635} \frac{0.05}{10^{-9}} \quad \text{(Equation 9)}$$

Analyzer device 102 determines a fading square error average for results given by Equation 8 using the algorithm given by Equation 10.

$$SE = \sum_{k=0}^{\infty} \lambda^k (a + b\,\sin(k\,w) + c\,\cos(k\,w) - y_k)^2 \quad \text{(Equation 10)}$$

In Equation 10, $\lambda^k$ is the discrete equivalent of the exponential decay function given by Equation 11.

$$\lambda = \frac{N-1}{N} \quad \text{(Equation 11)}$$

In Equation 11, N is a number of effective points or a filter constant. Analyzer device 102 performs a maximum likelihood process to determine values for a, b, and c. More specifically, analyzer device 102 attempts to minimize the fading square error average, SE, shown by Equation 10, by requiring the first derivatives against the parameters a, b, and c to be zero, as shown in Equation 12.

$$\frac{\partial}{\partial a} SE = \frac{\partial}{\partial b} SE = \frac{\partial}{\partial c} SE \quad \text{(Equation 12)}$$

In particular, analyzer device 102 uses the following linear system of equations, shown by Equations 13 and 14.

$$Y = MP \quad \text{(Equation 13)}$$

$$P = \begin{pmatrix} a \\ b \\ c \end{pmatrix} \quad \text{(Equation 14)}$$

Equation 15 expresses Y, and Equation 16 expresses M, as follows.

$$Y = \begin{pmatrix} \sum_{k=0}^{\infty} \lambda^k y_k \\ \sum_{k=0}^{\infty} \lambda^k \sin(wk) y_k \\ \sum_{k=0}^{\infty} \lambda^k \cos(wk) y_k \end{pmatrix} \quad \text{(Equation 15)}$$

$$M = \begin{pmatrix} \sum_{k=0}^{\infty} \lambda^k & \sum_{k=0}^{\infty} \lambda^k \sin(wk) & \sum_{k=0}^{\infty} \lambda^k \cos(wk) \\ \sum_{k=0}^{\infty} \lambda^k \sin(wk) & \sum_{k=0}^{\infty} \lambda^k \sin^2(wk) & \sum_{k=0}^{\infty} \lambda^k \sin(wk)\cos(wk) \\ \sum_{k=0}^{\infty} \lambda^k \cos(wk) & \sum_{k=0}^{\infty} \lambda^k \sin(wk)\cos(wk) & \sum_{k=0}^{\infty} \lambda^k \cos^2(wk) \end{pmatrix} \quad \text{(Equation 16)}$$

Further, analyzer device 102 uses the following Euler expression for trigonometric functions, as given by Equations 17 and 18.

$$\sin(wk) = \frac{e^{i\omega k} - e^{-i\omega k}}{2i} \quad \text{(Equation 17)}$$

$$\cos(wk) = \frac{e^{i\omega k} + e^{-i\omega k}}{2} \quad \text{(Equation 18)}$$

The symmetric matrix, M, can be expressed using Equation 19.

$$M = \begin{pmatrix} m_{00} & m_{01} & m_{02} \\ m_{01} & m_{11} & m_{12} \\ m_{02} & m_{12} & m_{22} \end{pmatrix} \quad \text{(Equation 19)}$$

Analyzer device 102 uses poly-logarithmic functions to derive the following formulas for the components of symmetric matrix, M.

$$m_{00} = \frac{1}{1-\lambda} \quad \text{(Equation 20)}$$

$$m_{11} = \frac{\lambda(1+\lambda)\sin^2(w)}{(1-\lambda)(1+\lambda^2 - 2\lambda\cos(2w))} \quad \text{(Equation 21)}$$

$$m_{22} = \frac{3 - \lambda + \frac{(1+\lambda)(1-\lambda)^2}{1+\lambda^2 - 2\lambda\cos(2w)}}{4(1-\lambda)} \quad \text{(Equation 22)}$$

$$m_{01} = -\frac{\lambda \sin(w)}{1+\lambda^2 - 2\lambda\cos(2w)} \quad \text{(Equation 23)}$$

$$m_{02} = \frac{1 - \lambda\cos(w)}{1+\lambda^2 - 2\lambda\cos(2w)} \quad \text{(Equation 24)}$$

$$m_{12} = -\frac{\lambda\sin(2w)}{2(1+\lambda^2 - 2\lambda\cos(2w))} \quad \text{(Equation 25)}$$

Using the sin and cos of the sum of angles, the following formula holds.

$$Y = \begin{pmatrix} \sum_{k=0}^{\infty} \lambda^k y_k \\ \sum_{k=0}^{\infty} \lambda^k \sin(wk) y_k \\ \sum_{k=0}^{\infty} \lambda^k \cos(wk) y_k \end{pmatrix} \quad \text{(Equation 26)}$$

$$= y_0 \begin{pmatrix} 1 \\ 0 \\ 1 \end{pmatrix} + \begin{pmatrix} \sum_{k=0}^{\infty} \lambda^k y_{k+1} \\ \sum_{k=0}^{\infty} \lambda^k \sin(w(k+1)) y_{k+1} \\ \sum_{k=0}^{\infty} \lambda^k \cos(w(k+1)) y_{k+1} \end{pmatrix}$$

$$= y_0 \begin{pmatrix} 1 \\ 0 \\ 1 \end{pmatrix} + \lambda T \tilde{Y}$$

In Equation 26, 1) is the $\tilde{Y}$ corresponding to the data with one less sample. More specifically, $y_0$ is missing and T is given by Equation 27.

$$T = \begin{pmatrix} 1 & 0 & 0 \\ 0 & \cos(w) & \sin(w) \\ 0 & -\sin(w) & \cos(w) \end{pmatrix} \quad \text{(Equation 27)}$$

Using the formula, Y=MP, shown in Equation 13, analyzer device 102 determines the following, given by Equation 28.

$$MP = Y \quad \text{(Equation 28)}$$

$$= y_0 \begin{pmatrix} 1 \\ 0 \\ 1 \end{pmatrix} + \lambda T \tilde{Y}$$

$$= y_0 \begin{pmatrix} 1 \\ 0 \\ 1 \end{pmatrix} + \lambda TMM^{-1}\tilde{Y}$$

$$= y_0 \begin{pmatrix} 1 \\ 0 \\ 1 \end{pmatrix} + \lambda TM\tilde{P}$$

Analyzer device 102 solves for $\tilde{P}$ as shown by Equation 29.

$$\tilde{P} = \frac{1}{\lambda} M^{-1} T^{-1} \left( MP - y_0 \begin{pmatrix} 1 \\ 0 \\ 1 \end{pmatrix} \right) \quad \text{(Equation 29)}$$

By substituting $y_0$ with $y_n$ and entries of P with the index n−1, analyzer device 102 determines the following, given by Equation 30.

$$\tilde{P} = TP + U(y_n - a_{n-1} - c_{n-1}) \quad \text{(Equation 30)}$$

In Equation 30, T and U are given by Equations 31 and 32, respectively.

$$T = \begin{pmatrix} 1 & 0 & 0 \\ 0 & \cos(w) & \sin(w) \\ 0 & -\sin(w) & \cos(w) \end{pmatrix} \quad \text{(Equation 31)}$$

$$U = \frac{1}{2N^3} \begin{pmatrix} 2N(N-1) + \frac{1}{1-\cos(w)} \\ -(2N-1)\frac{2\cos(w)+1}{\sin(w)} \\ 2 + 4N(N-1) - \frac{1}{1-\cos(w)} \end{pmatrix} \quad \text{(Equation 32)}$$

In at least some implementations, the initial $P_1$ is taken with a=500, b=0, and c=0. Additionally, T and U are fixed matrices and only the vector P is updated at each step, based on the new input $y_n$.

Figure 12:
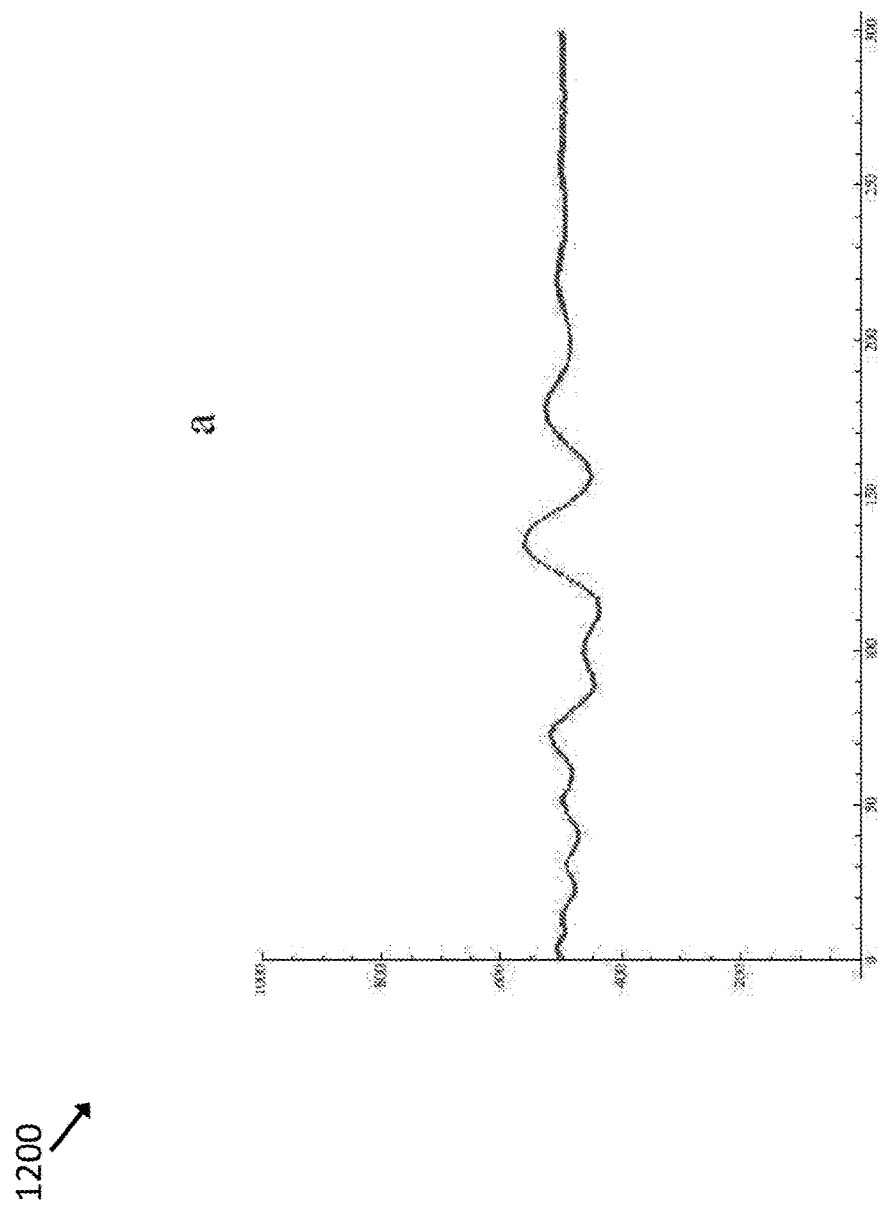
FIG. 12 is a plot of values of a parameter as the system of FIG. 1 executes an infinite response filter.
Figure 13:
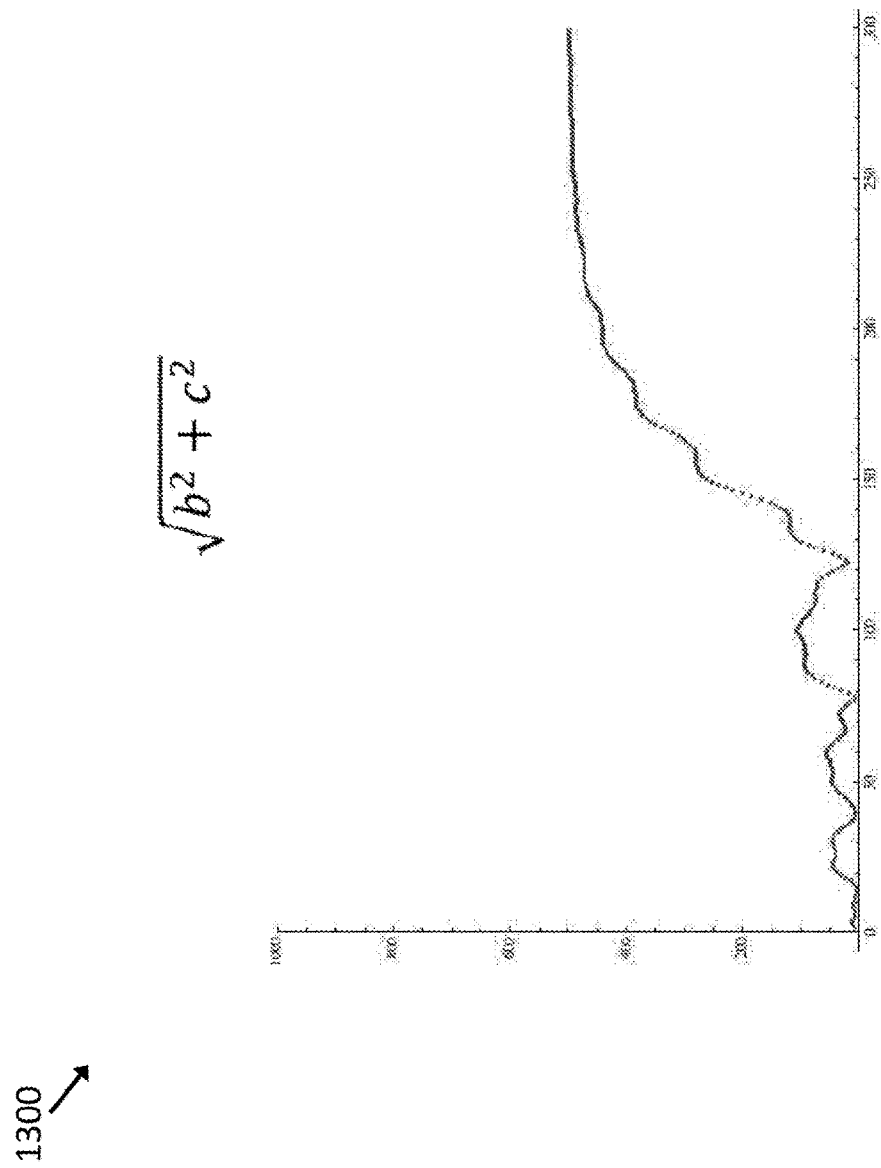
FIG. 13 is a plot of values of additional parameters as the system of FIG. 1 executes the infinite response filter.

FIG. 12 is a plot 1200 of values of parameter a as analyzer device 102 applies the infinite response filter 215 associated with Equation 8. FIG. 13 is a plot 1300 of the values of $\sqrt{(b^2+c^2)}$ as analyzer device 102 applies the infinite response filter 215 associated with Equation 8. While the value of a remains at approximately 500 as over the three hundred samples 144, the value of $\sqrt{(b^2+c^2)}$ grows from approximately zero and stabilizes at approximately 500. The parameters, b and c, define a harmony, and a vector created by the values of parameters, b and c, becomes more reliable as the vector grows.

Figure 14:
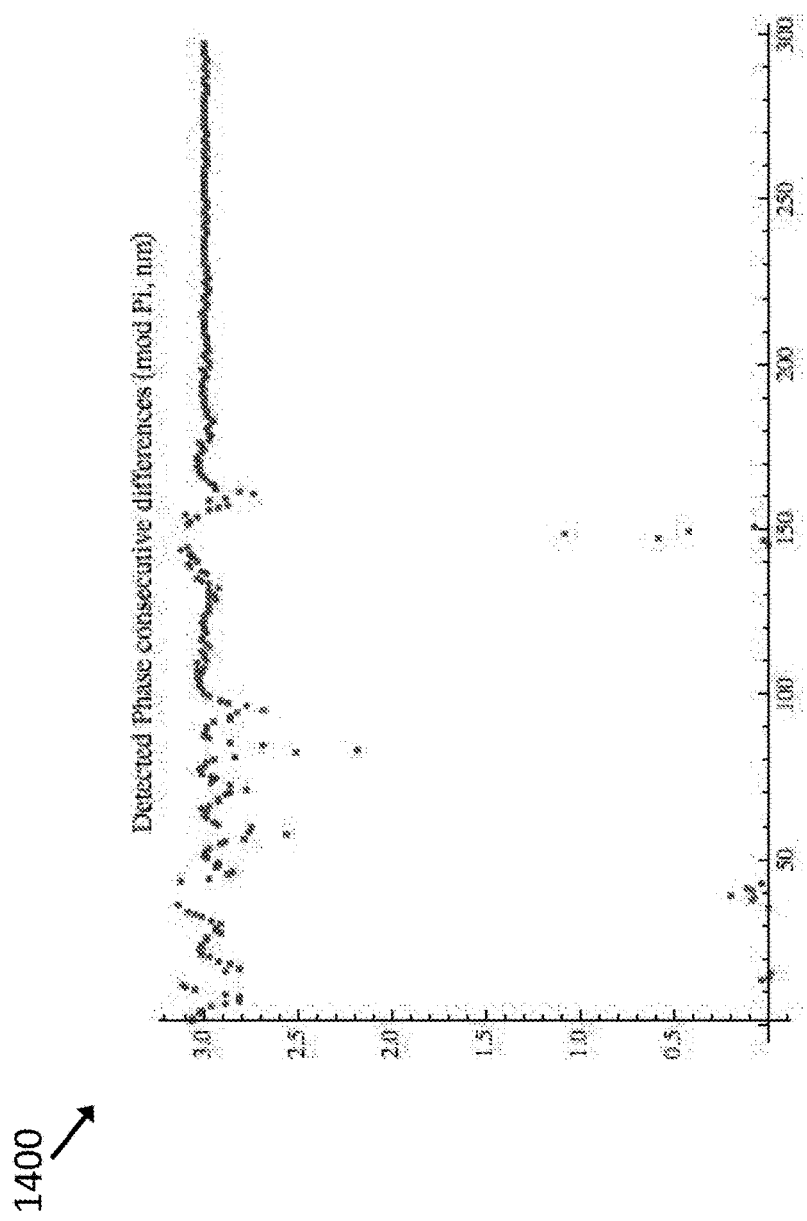
FIG. 14 is a plot of detected phase consecutive differences in nanometers as the system of FIG. 1 executes the infinite response filter.
Figure 15:
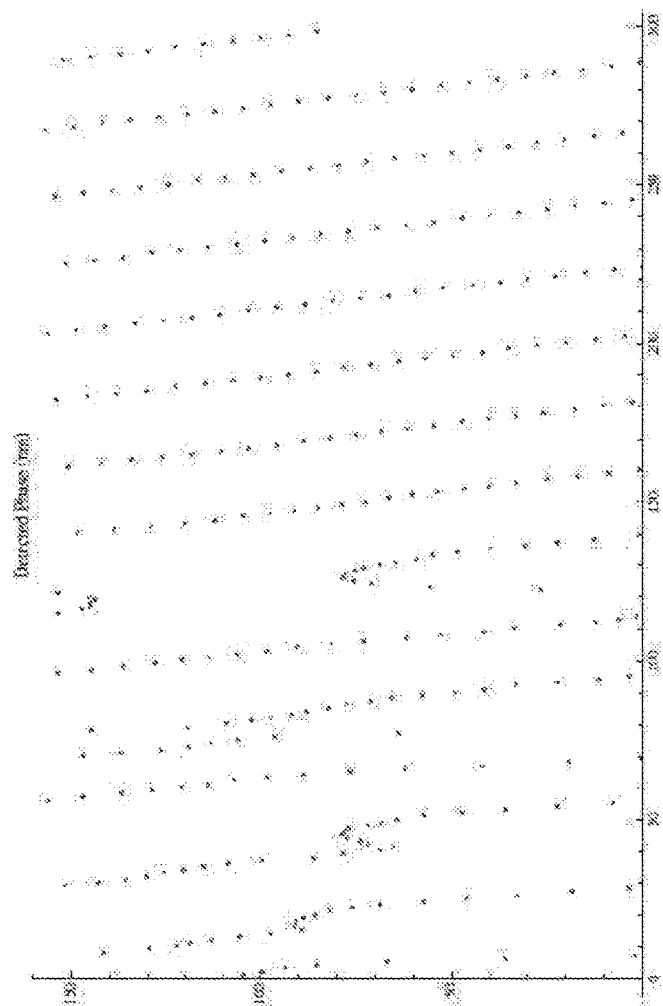
FIG. 15 is a plot of detected phase in nanometers, as the system of FIG. 1 executes the infinite response filter.

FIG. 14 is a plot 1400 of detected phase consecutive differences in nanometers, as analyzer device 102 executes the infinite response filter 215. More specifically, FIG. 14 is a plot 1400 of arctan [c/b]. FIG. 15 is a plot 1500 of detected phase in nanometers, as analyzer device 102 executes the infinite response filter 215. More specifically, FIG. 15 is a plot 1500 that represents a difference in nanometers of arctan [c/b]. By determining differences of consecutive phase estimates, analyzer device 102 detects a moment when the measurements are stabilized.

Figure 16:
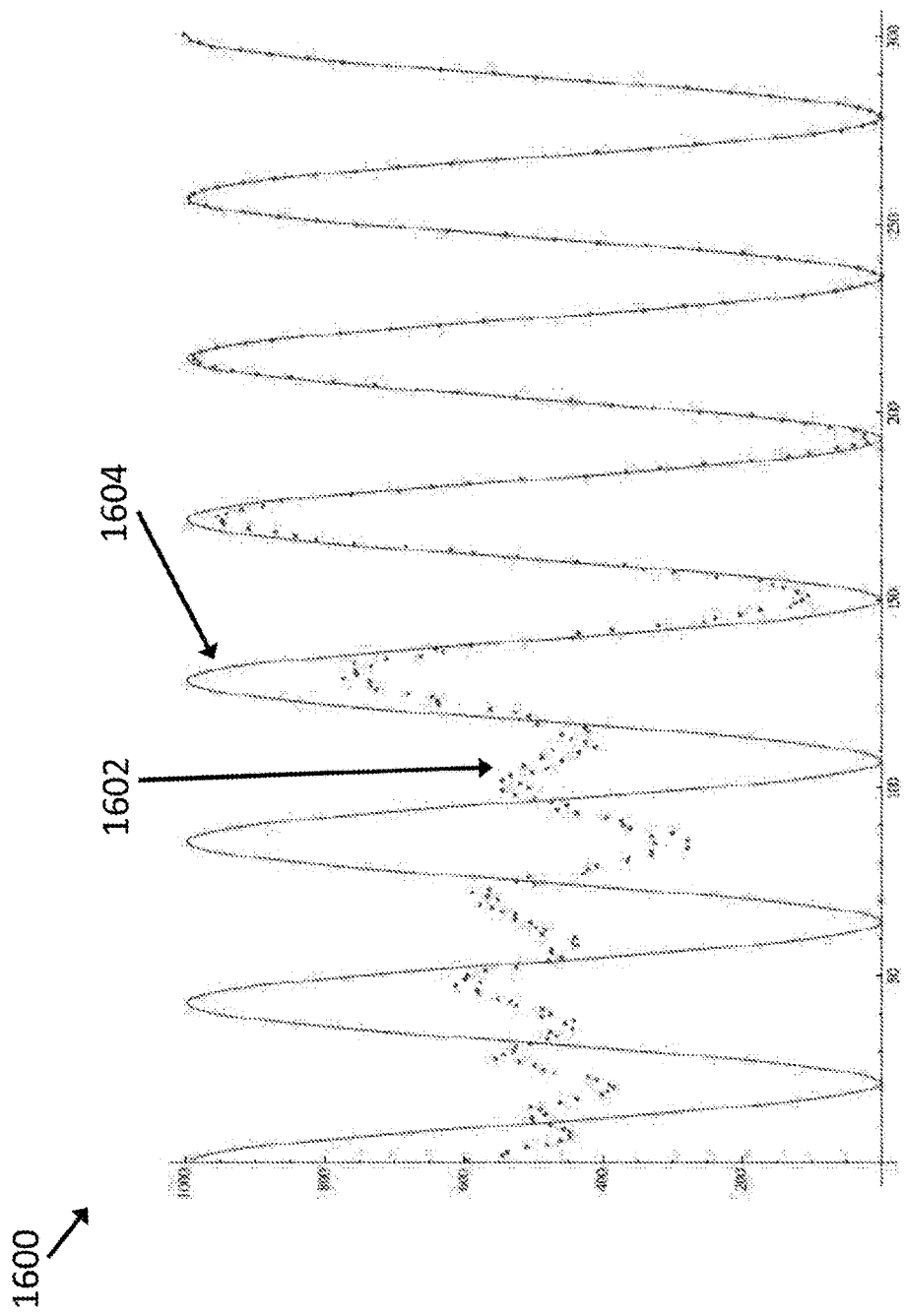
FIG. 16 is a plot of an exposed signal and a fitted signal generated by the system of FIG. 1 using the infinite response filter.

FIG. 16 is a plot 1600 of an exposed signal 1602 and a fitted signal 1604 generated by analyzer device 102 using infinite response filter 215, as described above. Fitted signal 1604 is fitted to exposed signal 1602 based on three hundred samples 144.

Figure 17:
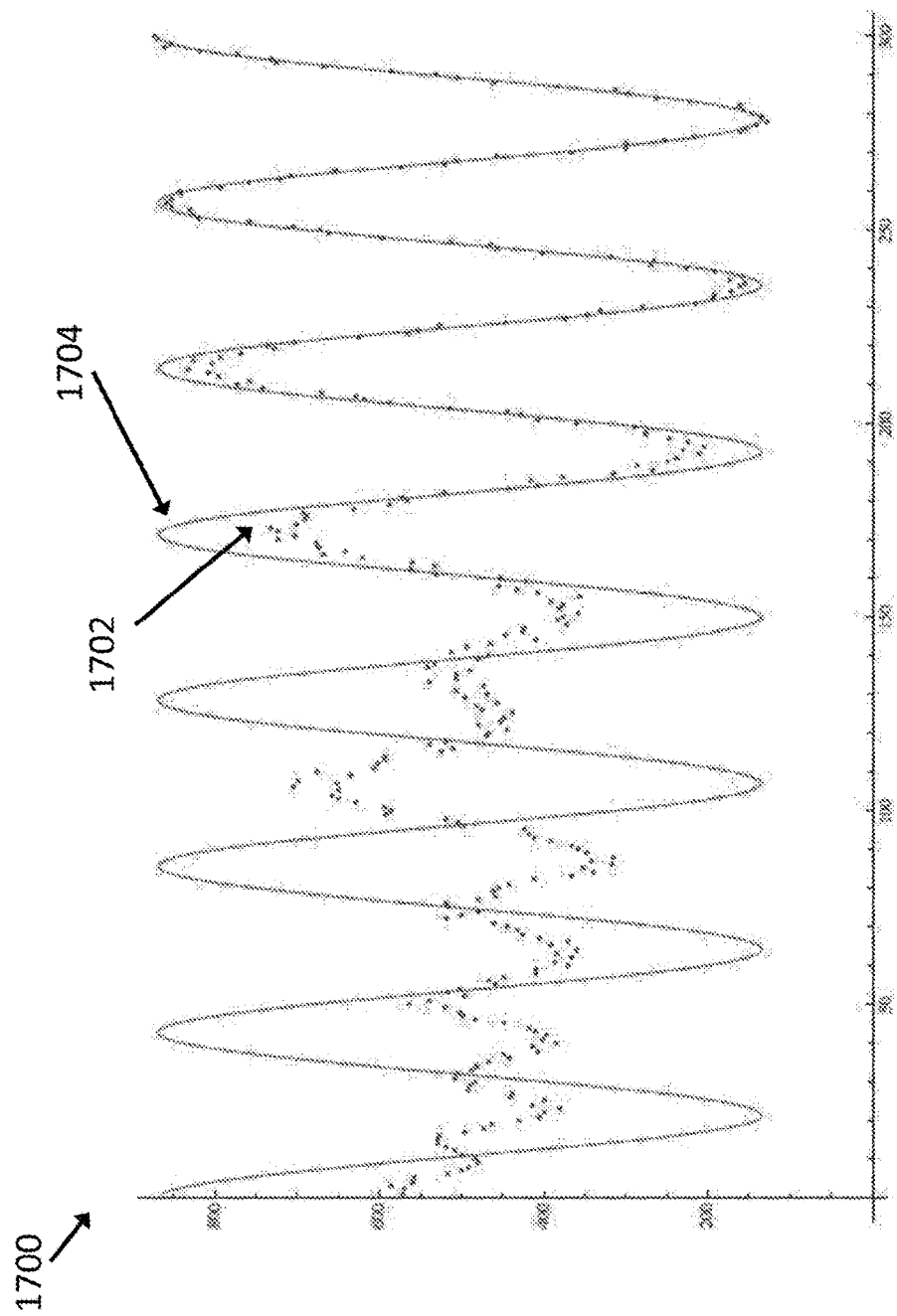
FIG. 17 is a plot of an exposed signal converging on a constant vibration, and a fitted signal generated by the system of FIG. 1 using the infinite response filter.

The process of applying infinite response filter 215 described above also works in the case of decaying vibrations that converge to a constant vibration, for example of amplitude 50 nanometers. All parameters remain the same as in the description above, with added convergence to a constant vibration of 50 nanometer amplitude. FIG. 17 is a plot 1700 of an exposed signal 1702 converging on the constant vibration, and a fitted signal 1704 generated by analyzer device 102 using the infinite response filter 215 described above.

Figure 18:
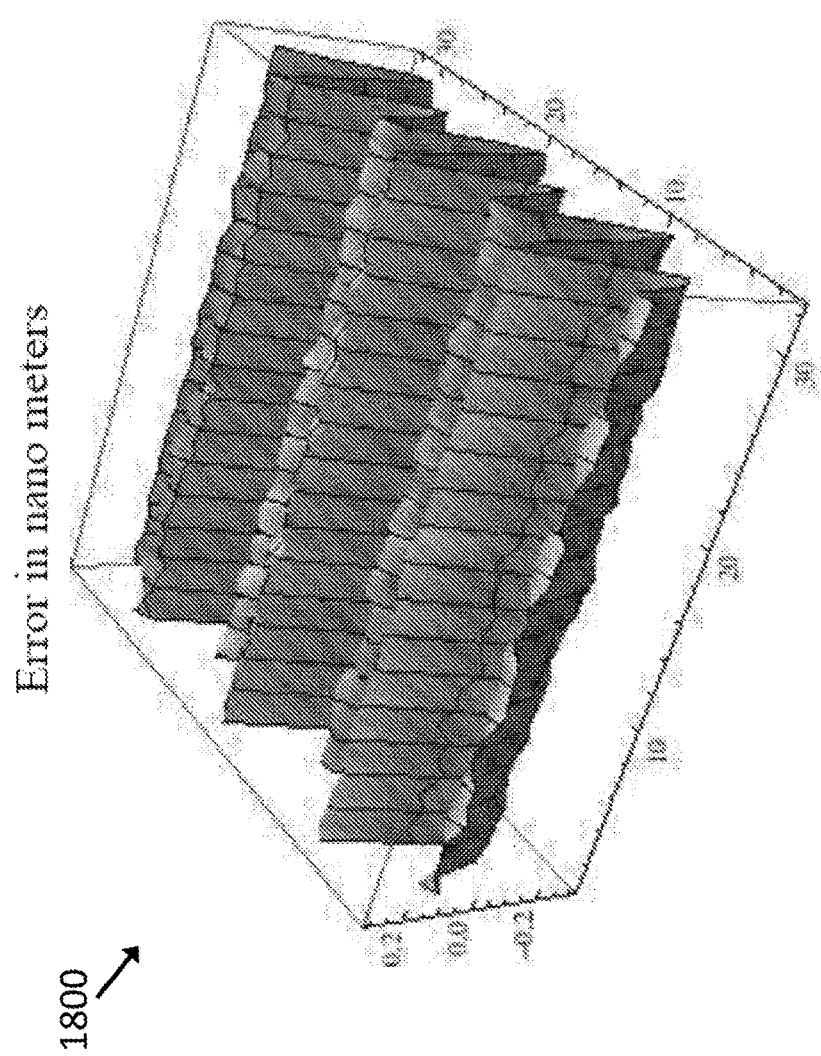
FIG. 18 is a three dimensional graph of errors between an estimated topology, generated using the infinite response filter, and an actual topology of the surface of the wafer.

FIG. 18 is a three dimensional graph 1800 of errors between an estimated topology, generated using the infinite response filter 215, and an actual topology of the surface 125 of the wafer 124. As shown, the errors are between −0.2 and 0.2 nanometers. In addition to providing smaller error than the moving window process 213, the infinite response filter 215 is computationally efficient. More specifically, at each step, while a new image (e.g., samples 144 associated with each light sensor 123 of image capture device 122) is acquired (e.g., received by analyzer device 102 in image signal 142), for each pixel 125, analyzer device 102 performs relatively non-computationally intensive operations to update parameters a, b, and c. Additionally, when changes in the inverse tangent of (c/b) are less than a predefined threshold, analyzer device 102 determines that system 100 should stop generating samples, as the reliability of the fitted signals 214 has become constant. Additionally, infinite response filter 215 may be executed in parallel on a plurality of computing devices, processors, or processing cores, for example one for each pixel 125.

Figure 19:
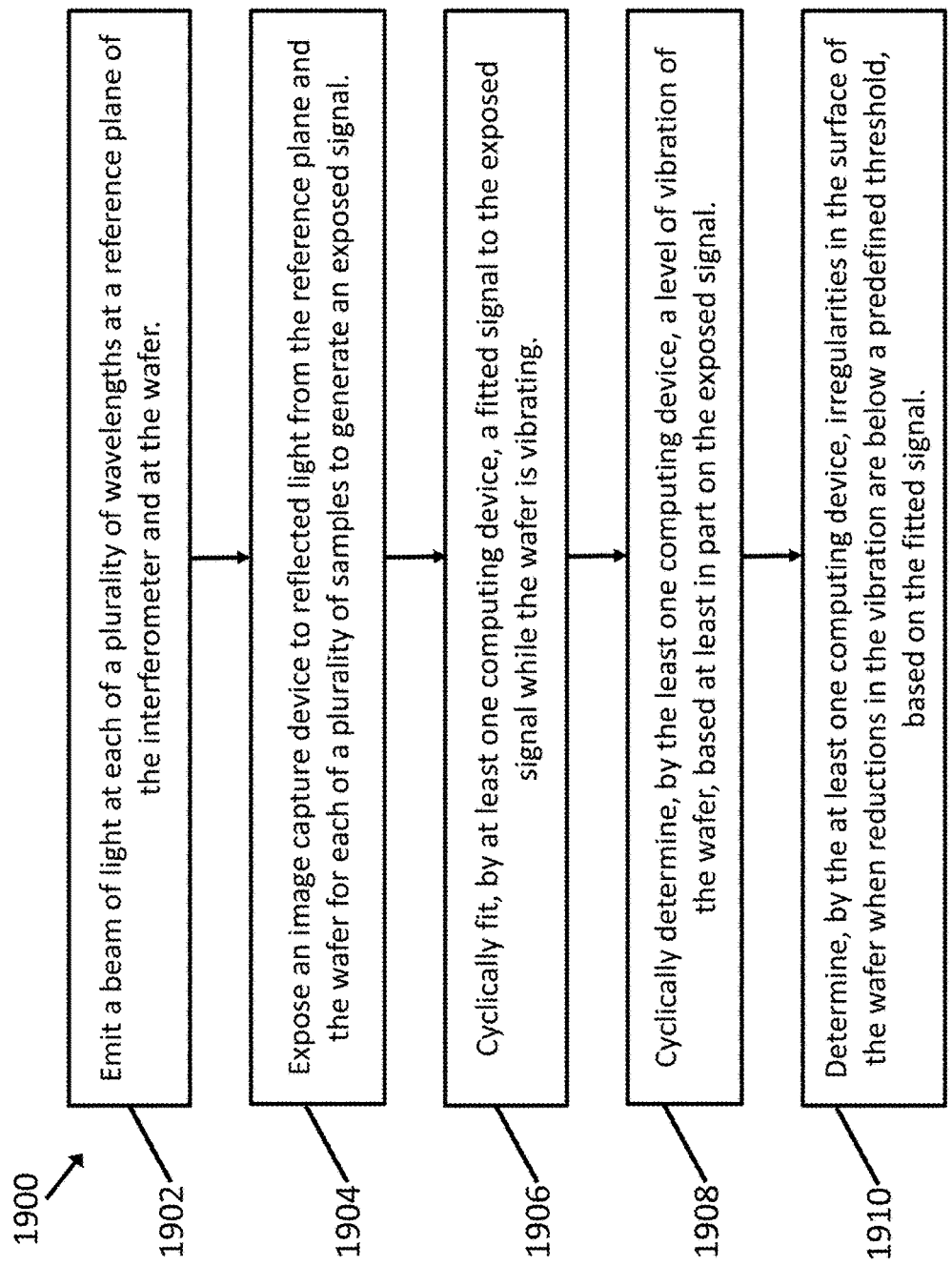
FIG. 19 is a diagram of a process carried out by the system of FIG. 1 for performing phase shift interferometry to detect irregularities of the surface of the wafer after the wafer has been placed into an interferometer and while the wafer is vibrating.

FIG. 19 is a diagram of a process 1900 carried out by system 100 for performing phase shift interferometry to detect irregularities 230 of the surface 125 of wafer 124 after wafer 124 has been placed into interferometer 110 and while wafer 124 is vibrating. Process 1900 includes emitting 1902 a beam of light 113 at each of a plurality of wavelengths (e.g., wavelengths 130) at a reference plane 118 of interferometer 110 and at wafer 124. Additionally, process 1900 includes exposing 1904 an image capture device 122 to reflected light 117 from the reference plane 118 and the wafer 124 for each of a plurality of captured image samples (e.g., samples 144), to generate an exposed signal 206. The reflected light 117 is a fringe pattern. In other implementations, a moving fringe pattern (i.e., the fringe pattern is being translated in a direction such as up, down, left, or right) is projected onto the surface 125 of wafer 124 and image capture device 122 is exposed to the moving fringe pattern for each of a plurality of captured image samples (e.g., samples 144) to generate the exposed signal 206. Additionally, process 1900 includes cyclically fitting 1906, by at least one computing device (e.g., one or more computing devices 104, 106, and/or 108 of analyzer device 102), a fitted signal 214 to the exposed signal 206 while the wafer 124 is vibrating. Additionally, process 1900 includes cyclically determining 1908, by the at least one computing device (e.g., one or more computing devices 104, 106, and/or 108 of analyzer device 102), a level of vibration (e.g., amplitude 223) of the wafer 124, based at least in part on the exposed signal (e.g., exposed signal 206). Additionally, process 1900 includes determining 1910, by the at least one computing device (e.g., one or more computing devices 104, 106, and/or 108 of analyzer device 102), irregularities 230 in the surface 125 of the wafer 124 when reductions in the vibration 222 are below a predefined threshold 224, based on the fitted signal 214.

In some implementations, process 1900 includes exposing image capture device 122 to reflected light 117 from the reference plane 118 and the wafer 124 for a predefined period of time (e.g., exposure time 140) for each of the plurality of captured image samples (e.g., samples 144), to generate exposed signal 206. In some implementations, process 1900 includes exposing image capture device 122 to the moving fringe pattern for a predefined period of time (e.g., exposure time 140) for each of the plurality of captured image samples (e.g., samples 144), to generate exposed signal 206. In some implementations, the captured image samples 144 are acquired at a nearly (i.e., substantially) constant temporal rate to generate exposed signal 206. In some implementations, process 1900 additionally includes replacing the wafer 124 with a second wafer 124 when reductions in the vibration 222 are below the predefined threshold 224, and before determining irregularities 230 in the surface 125 of the wafer 124. In some implementations, determining the level of vibration (e.g., amplitude 223) further includes determining a rate of change in a phase (change in phase 209 and/or change in phase 217) between the plurality of samples 144. In some implementations, the fitted signal 214 is one of a plurality of fitted signals 214 and each fitted signal 214 corresponds to one of a plurality of pixels 125. In such implementations, determining irregularities 230 in the surface 125 further includes generating a fringe image 228 based on the plurality of fitted signals 214. In some implementations, the exposed signal 206 is one of a plurality of exposed signals 206 and each exposed signal 206 corresponds to one of a plurality of pixels 125. In such implementations, fitting the fitted signal 214 further includes fitting each of a plurality of fitted signals 214 to each of the plurality of exposed signals 206 in parallel.

In some implementations, fitting the fitted signal 214 further comprises performing a maximum likelihood Fourier fit. In some implementations, process 1900 additionally includes performing a Fourier analysis on a first contiguous set (e.g., window 606 at first position 610) of the samples 144 and performing a partial Fourier integral on a second contiguous set (e.g., window 606 at second position 612) of the samples 144 that includes a portion of the first contiguous set of the samples (e.g., 280 samples from window 606 at first position 610) and additional samples (e.g., twenty later samples 144) collected after the first contiguous set. In some implementations, fitting the fitted signal 214 further includes applying an infinite response filter 215 to the exposed signal 206. In some implementations, process 1900 includes fitting the fitted signal 214 according to a form: a+b sin(4πG/λi)+c cos(4πG/λi). In some implementations, process 1900 includes fitting the fitted signal 214 according to a form: a+(1−de$^{-i/\tau}$) [b sin(4πG/λi)+c cos(4πG/λi)]. In some implementations, process 1900 includes fitting the fitted signal 214 according to a form: y=a+b sin(kw)+c cos(kw).

A technical effect of systems and methods described herein includes at least one of: (a) emitting a beam of light at each of a plurality of wavelengths at a reference plane of an interferometer and at a wafer; (b) exposing an image capture device to reflected light from the reference plane and the wafer for each of a plurality of captured image samples to generate an exposed signal; (c) cyclically fitting, by at least one computing device, a fitted signal to the exposed signal while the wafer is vibrating; (d) cyclically determining, by the least one computing device, a level of vibration of the wafer, based at least in part on the exposed signal; and (e) determining, by the at least one computing device, irregularities in the surface of the wafer when reductions in the vibration are below a predefined threshold, based on the fitted signal.

As compared to known systems and methods for performing phase shift interferometry, the systems and methods described herein enable precise, accurate, and more computationally efficient detection of irregularities on the surface of an object such as a wafer, even while the wafer is vibrating. Accordingly, delays normally incurred to wait for a wafer to stop vibrating before detecting irregularities in the surface can be avoided or reduced, and a total number of wafers measured during a given time period can be increased.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A method for performing phase shift interferometry to detect irregularities of a surface of a wafer after the wafer has been placed into an interferometer and while the wafer is vibrating, said method comprising the steps of:
    emitting a beam of light at each of a plurality of wavelengths at a reference plane of the interferometer and at the wafer;
    exposing an image capture device to reflected light from the reference plane and the wafer for each of a plurality of captured image samples to generate an exposed signal;
    cyclically fitting, by at least one computing device, a fitted signal to the exposed signal while the wafer is vibrating;
    cyclically determining, by the at least one computing device, a level of vibration of the wafer, based at least in part on the exposed signal; and
    determining, by the at least one computing device, irregularities in the surface of the wafer when reductions in the vibration are below a predefined threshold, based on the fitted signal.

2. The method of claim 1, wherein the wafer is a first wafer, said method further comprising replacing the first wafer with a second wafer when reductions in the vibration are below the predefined threshold and before determining irregularities in the surface of the first wafer.

3. The method of claim 1, wherein determining the level of vibration further comprises determining a rate of change in a phase between the plurality of samples.

4. The method of claim 1, wherein the fitted signal is one of a plurality of fitted signals, each fitted signal corresponding to one of a plurality of pixels, and determining irregularities in the surface further comprises generating a fringe image based on the plurality of fitted signals.

5. The method of claim 1, wherein the exposed signal is one of a plurality of exposed signals, each exposed signal corresponding to one of a plurality of pixels, and fitting the fitted signal further comprises fitting each of a plurality of fitted signals to each of the plurality of exposed signals in parallel.

6. The method of claim 1, wherein fitting the fitted signal further comprises performing a maximum likelihood Fourier fit.

7. The method of claim 1, further comprising:
    performing a Fourier analysis on a first contiguous set of the samples; and
    performing a partial Fourier integral on a second contiguous set of the samples that includes a portion of the first contiguous set of the samples and additional samples collected after the first contiguous set.

8. The method of claim 1, wherein fitting the fitted signal further comprises applying an infinite response filter to the exposed signal.

9. The method of claim 1, further comprising fitting the fitted signal according to a form:

$$a+b\,\sin(4\pi G/\lambda i)+c\,\cos(4\pi G/\lambda i).$$

10. The method of claim 1, further comprising fitting the fitted signal according to a form:

$$a+(1-de^{-i/\tau})[b\,\sin(4\pi G/\lambda i)+c\,\cos(4\pi G/\lambda i)].$$

11. The method of claim 1, further comprising fitting the fitted signal according to a form:

$$y=a+b\,\sin(kw)+c\,\cos(kw).$$

12. The method of claim 1, wherein emitting the beam of light further comprises controlling a change in the wavelengths as a function of at least one of time and a sample number.

13. A system comprising at least one computing device coupled to an interferometer including a light source, a reference plane located opposite said light source, a beam splitter located between said light source and said reference plane, and an image capture device configured to receive light from said beam splitter, said at least one computing device configured to perform phase shift interferometry to detect irregularities of a surface of a wafer after the wafer has been placed into said interferometer and while the wafer is vibrating, by:
    causing said light source to emit a beam of light at each of a plurality of wavelengths at said reference plane and at the wafer;
    causing said image capture device to be exposed to reflected light from the reference plane and the wafer for each of a plurality of captured image samples to generate an exposed signal;
    cyclically fitting a fitted signal to the exposed signal while the wafer is vibrating;
    cyclically determining a level of vibration of the wafer, based at least in part on the exposed signal; and
    determining irregularities in the surface of the wafer when reductions in the vibration are below a predefined threshold, based on the fitted signal.

14. The system of claim 13, wherein said at least one computing device is further configured to determine the level of vibration by determining a rate of change in a phase between the plurality of samples.

15. The system of claim 13, wherein the fitted signal is one of a plurality of fitted signals, each fitted signal corresponding to one of a plurality of pixels, and said at least one computing device is further configured to generate a fringe image based on the plurality of fitted signals.

16. The system of claim 13, wherein the exposed signal is one of a plurality of exposed signals, each exposed signal corresponding to one of a plurality of pixels, and said at least one computing device is further configured to fit each of a plurality of fitted signals to each of the plurality of exposed signals in parallel.

17. The system of claim 13, wherein said at least one computing device is further configured such that fitting the fitted signal includes performing a maximum likelihood Fourier fit.

18. The system of claim 13, wherein said at least one computing device is further configured to:
perform a Fourier analysis on a first contiguous set of the samples; and
perform a partial Fourier integral on a second contiguous set of the samples that includes a portion of the first contiguous set of the samples and additional samples collected after the first contiguous set.

19. The system of claim 13, wherein said at least one computing device is further configured such that fitting the fitted signal further comprises applying an infinite response filter to the exposed signal.

20. A method for detecting irregularities of a surface of an object while the object is vibrating, said method comprising the steps of:
projecting a moving fringe pattern to the surface of the object;
exposing an image capture device to the moving fringe pattern for each of a plurality of captured image samples to generate an exposed signal;
cyclically fitting, by at least one computing device, a fitted signal to the exposed signal while the object is vibrating;
cyclically determining, by the at least one computing device, a level of vibration of the object, based at least in part on the exposed signal; and
determining, by the at least one computing device, irregularities in the surface when reductions in the vibration are below a predefined threshold, based on the fitted signal.

* * * * *